(12) United States Patent
Blott et al.

(10) Patent No.: US 9,446,178 B2
(45) Date of Patent: Sep. 20, 2016

(54) WOUND CLEANSING APPARATUS IN-SITU

(75) Inventors: Patrick Lewis Blott, York (GB); Bryan Greener, York (GB); Edward Yerbury Hartwell, Hull (GB); Derek Nicolini, Hull (GB); Tina Michelle Walker, York (GB); Julian Lee-Webb, York (GB)

(73) Assignee: Smith & Nephew PLC, London (GB)

( * ) Notice: Subject to any disclaimer, the term of this patent is extended or adjusted under 35 U.S.C. 154(b) by 0 days.

(21) Appl. No.: 13/212,039

(22) Filed: Aug. 17, 2011

(65) Prior Publication Data
US 2012/0041399 A1 Feb. 16, 2012

Related U.S. Application Data

(63) Continuation of application No. 12/940,788, filed on Nov. 5, 2010, which is a continuation of application No. 10/575,871, filed as application No. PCT/GB2004/004549 on Oct. 28, 2004, now Pat. No. 7,964,766.

(30) Foreign Application Priority Data

Oct. 28, 2003 (GB) .................................. 0325129.5

(51) Int. Cl.
*A61F 13/02* (2006.01)
*A61M 1/00* (2006.01)
(Continued)

(52) U.S. Cl.
CPC ...... *A61M 1/0088* (2013.01); *A61F 13/00068* (2013.01); *A61F 13/0216* (2013.01);
(Continued)

(58) Field of Classification Search
CPC ............. A61M 1/0088; A61M 27/00; A61M 1/0023; A61M 2001/0052; A61F 2013/00536; A61F 13/02; A61F 13/0203; A61F 2013/00119; A61F 2013/00748
USPC ....... 602/41–43; 424/443–449, 78.05, 78.06, 424/78.07; 604/304, 307, 289, 313
See application file for complete search history.

(56) References Cited

U.S. PATENT DOCUMENTS

| 695,270 A | 3/1902 | Beringer |
|---|---|---|
| 765,746 A | 7/1904 | Miner |

(Continued)

FOREIGN PATENT DOCUMENTS

| CA | 2369000 A1 | 10/1990 |
|---|---|---|
| CA | 2103033 C | 11/1992 |

(Continued)

OTHER PUBLICATIONS

US 6,306,115, 10/2001, Kelly et al. (withdrawn).
(Continued)

*Primary Examiner* — Ophelia A Hawthorne
(74) *Attorney, Agent, or Firm* — Knobbe, Martens, Olson & Bear LLP

(57) ABSTRACT

An apparatus for cleansing wounds, in which wound exudate is removed from a wound bed and selectively cleansed and returned to the wound. The cleansing means removes materials deleterious to wound healing, and the cleansed fluid, still containing materials that are beneficial in promoting wound healing, is returned to the wound bed. The associated wound dressing and cleansing means are conformable to the wound, and may have irrigant fluid circulated from a reservoir by a device for moving fluid through a flow path which passes through the dressing and a means for fluid cleansing and back to the dressing.

29 Claims, 7 Drawing Sheets

(51) Int. Cl.
  *A61M 3/02* (2006.01)
  *A61M 35/00* (2006.01)
  *A61F 13/00* (2006.01)
  *A61M 27/00* (2006.01)

(52) U.S. Cl.
  CPC .......... *A61F13/0259* (2013.01); *A61M 1/009* (2014.02); *A61M 1/0058* (2013.01); *A61M 1/0068* (2014.02); *A61M 1/0072* (2014.02); *A61M 1/0084* (2013.01); *A61M 3/0229* (2013.01); *A61M 35/00* (2013.01); *A61F 2013/00357* (2013.01); *A61M 1/0037* (2013.01); *A61M 1/0062* (2013.01); *A61M 27/00* (2013.01); *A61M 2205/075* (2013.01); *A61M 2205/106* (2013.01); *A61M 2205/7518* (2013.01); *A61M 2205/8206* (2013.01); *Y10T 29/49826* (2015.01)

(56) References Cited

U.S. PATENT DOCUMENTS

| | | |
|---|---|---|
| 846,674 A | 7/1907 | Funk |
| 1,355,679 A | 10/1920 | McConnell |
| 1,355,846 A | 10/1920 | Rannells |
| 1,385,346 A | 7/1921 | Taylor |
| 1,480,562 A | 1/1924 | Mock |
| 1,585,104 A | 5/1926 | Montgomery |
| 1,732,310 A | 12/1929 | Naibert |
| 1,863,534 A | 6/1932 | Odell |
| 1,936,129 A | 11/1933 | Fisk |
| 2,122,121 A | 6/1938 | Tillotson |
| 2,232,254 A | 2/1941 | Morgan |
| 2,280,915 A | 4/1942 | Johnson |
| 2,338,339 A | 1/1944 | La Mere et al. |
| 2,366,799 A | 1/1945 | Luisada |
| 2,367,690 A | 1/1945 | Purdy |
| 2,547,758 A | 4/1951 | Keeling |
| 2,568,933 A | 9/1951 | Robbins |
| 2,632,443 A | 3/1953 | Lesher |
| 2,682,873 A | 7/1954 | Evans et al. |
| 2,910,763 A | 8/1955 | Lauterbach |
| 3,026,874 A | 11/1959 | Stevens |
| 2,969,057 A | 1/1961 | Simmons |
| 3,026,526 A | 3/1962 | Montrose |
| 3,042,041 A | 7/1962 | Jascalevich |
| 3,111,948 A | 11/1963 | Burgeni |
| 3,115,138 A | 12/1963 | McElvenny et al. |
| 3,217,707 A | 11/1965 | Werding |
| 3,238,937 A | 3/1966 | Stein |
| 3,286,711 A | 11/1966 | MacLeod |
| 3,315,665 A | 4/1967 | MacLeod |
| 3,334,626 A | 8/1967 | Schimmel |
| 3,364,931 A | 1/1968 | Hirsch |
| 3,367,332 A | 2/1968 | Groves |
| 3,465,748 A | 9/1969 | Kravchenko |
| 3,478,736 A | 11/1969 | Roberts et al. |
| 3,486,504 A | 12/1969 | Austin et al. |
| 3,568,675 A | 3/1971 | Harvey |
| 3,572,340 A | 3/1971 | Lloyd et al. |
| 3,610,238 A | 10/1971 | Rich et al. |
| 3,682,180 A | 8/1972 | McFarlane |
| 3,712,298 A | 1/1973 | Snowdon et al. |
| 3,787,882 A | 1/1974 | Fillmore et al. |
| 3,794,035 A | 2/1974 | Brenner |
| 3,809,086 A | 5/1974 | Schachet et al. |
| 3,826,254 A | 7/1974 | Mellor |
| 3,859,989 A | 1/1975 | Spielberg |
| 3,871,376 A | 3/1975 | Kozak |
| 3,872,862 A | 3/1975 | Hume |
| 3,874,387 A | 4/1975 | Barbieri |
| 3,896,810 A | 7/1975 | Akiyama |
| 3,908,664 A | 9/1975 | Loseff |
| 3,938,540 A | 2/1976 | Holbrook et al. |
| 3,954,105 A | 5/1976 | Nordby et al. |
| 3,961,625 A | 6/1976 | Dillon |
| 3,972,328 A | 8/1976 | Chen |
| 3,988,793 A | 11/1976 | Abitbol |
| 3,993,080 A | 11/1976 | Loseff |
| RE29,319 E | 7/1977 | Nordby et al. |
| 4,080,970 A | 3/1978 | Miller |
| 4,102,342 A | 7/1978 | Akiyama et al. |
| 4,112,947 A | 9/1978 | Nehring |
| 4,112,949 A | 9/1978 | Rosenthal et al. |
| 4,136,696 A | 1/1979 | Nehring |
| 4,149,541 A | 4/1979 | Gammons et al. |
| 4,169,563 A | 10/1979 | Leu |
| 4,172,455 A | 10/1979 | Beaussant |
| 4,184,510 A | 1/1980 | Murry et al. |
| 4,212,296 A | 7/1980 | Schaar |
| 4,217,894 A | 8/1980 | Franetzki |
| 4,219,019 A | 8/1980 | Coates |
| 4,224,945 A * | 9/1980 | Cohen .......................... 606/201 |
| 4,250,882 A | 2/1981 | Adair |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,297,995 A | 11/1981 | Golub |
| 4,316,466 A | 2/1982 | Babb |
| 4,373,519 A | 2/1983 | Errede et al. |
| 4,382,441 A | 5/1983 | Svedman |
| 4,392,853 A | 7/1983 | Muto |
| 4,419,097 A | 12/1983 | Rowland |
| 4,444,548 A | 4/1984 | Andersen et al. |
| 4,459,139 A | 7/1984 | vonReis et al. |
| 4,465,485 A | 8/1984 | Kashmer et al. |
| 4,468,227 A | 8/1984 | Jensen |
| 4,469,092 A | 9/1984 | Marshall et al. |
| 4,475,909 A | 10/1984 | Eisenberg |
| 4,480,638 A | 11/1984 | Schmid |
| 4,524,064 A | 6/1985 | Nambu |
| 4,525,166 A | 6/1985 | Laclerc |
| 4,527,064 A | 7/1985 | Anderson |
| 4,534,356 A | 8/1985 | Papadakis |
| 4,540,412 A | 9/1985 | Van Overloop |
| 4,543,100 A | 9/1985 | Brodsky |
| 4,551,141 A | 11/1985 | McNeil |
| 4,573,965 A | 3/1986 | Russo |
| 4,592,750 A | 6/1986 | Kay |
| 4,605,399 A | 8/1986 | Weston et al. |
| 4,608,041 A | 8/1986 | Nielsen |
| 4,624,656 A | 11/1986 | Clark et al. |
| 4,640,688 A | 2/1987 | Hauser |
| 4,643,641 A | 2/1987 | Clausen et al. |
| 4,655,754 A | 4/1987 | Richmond et al. |
| 4,655,766 A | 4/1987 | Theeuwes et al. |
| 4,681,562 A | 7/1987 | Beck et al. |
| 4,710,165 A | 12/1987 | McNeil et al. |
| 4,738,249 A | 4/1988 | Linman |
| 4,743,232 A | 5/1988 | Kruger |
| 4,753,231 A | 6/1988 | Lang et al. |
| 4,759,354 A | 7/1988 | Quarfoot |
| 4,764,167 A | 8/1988 | Tu |
| 4,765,316 A | 8/1988 | Marshall |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,813,931 A * | 3/1989 | Hauze ................. A61M 1/0001 600/573 |
| 4,820,265 A | 4/1989 | DeSatnick et al. |
| 4,820,284 A | 4/1989 | Hauri |
| 4,826,494 A | 5/1989 | Richmond et al. |
| 4,828,546 A | 5/1989 | McNeil et al. |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A | 6/1989 | Berg et al. |
| 4,846,164 A | 7/1989 | Martz |
| 4,851,545 A | 7/1989 | Song et al. |
| 4,863,449 A | 9/1989 | Therriault et al. |
| 4,878,901 A | 11/1989 | Sachse |

(56) References Cited

U.S. PATENT DOCUMENTS

| | | |
|---|---|---|
| 4,906,233 A | 3/1990 | Moriuchi et al. |
| 4,917,112 A | 4/1990 | Kalt |
| 4,921,488 A | 5/1990 | Maitz et al. |
| 4,921,492 A | 5/1990 | Schultz |
| 4,925,447 A | 5/1990 | Rosenblatt |
| 4,931,519 A | 6/1990 | Song et al. |
| 4,936,834 A | 6/1990 | Beck et al. |
| 4,941,882 A | 7/1990 | Ward et al. |
| 4,950,483 A | 8/1990 | Ksander et al. |
| 4,969,880 A | 11/1990 | Zamierowski |
| 4,969,881 A | 11/1990 | Viesturs |
| 4,972,829 A | 11/1990 | Knerr |
| 4,979,944 A | 12/1990 | Luzsicza |
| 4,990,137 A | 2/1991 | Graham |
| 4,994,022 A | 2/1991 | Steffler et al. |
| 4,997,438 A | 3/1991 | Nipper |
| 5,035,884 A | 7/1991 | Song et al. |
| 5,055,198 A | 10/1991 | Shettigar |
| 5,056,510 A | 10/1991 | Gilman |
| 5,071,409 A | 12/1991 | Rosenberg |
| 5,073,172 A | 12/1991 | Fell |
| 5,086,763 A | 2/1992 | Hathman |
| 5,086,764 A | 2/1992 | Gilman |
| 5,100,395 A | 3/1992 | Rosenberg |
| 5,100,396 A | 3/1992 | Zamierowski |
| 5,106,362 A | 4/1992 | Gilman |
| 5,106,629 A | 4/1992 | Cartmell et al. |
| 5,113,871 A | 5/1992 | Viljanto et al. |
| 5,115,472 A | 5/1992 | Park et al. |
| 5,141,503 A | 8/1992 | Sewell, Jr. |
| 5,149,331 A | 9/1992 | Ferdman et al. |
| 5,152,757 A | 10/1992 | Eriksson |
| 5,160,322 A | 11/1992 | Scheremet et al. |
| 5,160,328 A | 11/1992 | Cartmell et al. |
| 5,167,613 A | 12/1992 | Karami et al. |
| 5,176,663 A | 1/1993 | Svedman et al. |
| 5,178,157 A | 1/1993 | Fanlo |
| 5,184,077 A | 2/1993 | Day et al. |
| 5,195,977 A | 3/1993 | Pollitt |
| 5,197,945 A | 3/1993 | Cole et al. |
| 5,215,519 A | 6/1993 | Shettigar |
| 5,222,714 A | 6/1993 | Morinigo et al. |
| 5,228,431 A | 7/1993 | Giarretto |
| 5,234,419 A | 8/1993 | Bryant et al. |
| 5,238,732 A | 8/1993 | Krishnan |
| 5,261,893 A | 11/1993 | Zamierowski |
| 5,263,922 A | 11/1993 | Sova et al. |
| 5,266,928 A | 11/1993 | Johnson |
| 5,279,550 A | 1/1994 | Habib et al. |
| 5,279,608 A | 1/1994 | Cherif Cheikh |
| 5,307,791 A | 5/1994 | Senoue et al. |
| 5,328,614 A | 7/1994 | Matsumura |
| 5,336,219 A | 8/1994 | Krantz |
| 5,354,261 A | 10/1994 | Clark et al. |
| 5,358,494 A | 10/1994 | Svedman |
| 5,360,445 A | 11/1994 | Goldowsky |
| 5,362,543 A | 11/1994 | Nickerson |
| 5,364,381 A | 11/1994 | Soga et al. |
| 5,380,280 A | 1/1995 | Peterson |
| 5,380,294 A | 1/1995 | Persson |
| 5,437,651 A | 8/1995 | Todd et al. |
| 5,445,604 A | 8/1995 | Lang |
| 5,447,492 A | 9/1995 | Cartmell et al. |
| 5,456,660 A | 10/1995 | Reich et al. |
| 5,462,514 A | 10/1995 | Harris |
| D364,679 S | 11/1995 | Heaton et al. |
| 5,476,664 A | 12/1995 | Robinson et al. |
| 5,480,377 A | 1/1996 | Cartmell et al. |
| 5,484,427 A | 1/1996 | Gibbons |
| 5,489,280 A | 2/1996 | Russell |
| 5,492,313 A | 2/1996 | Pan et al. |
| 5,497,788 A | 3/1996 | Inman et al. |
| 5,498,338 A | 3/1996 | Kruger et al. |
| 5,527,293 A | 6/1996 | Zamierowski |
| 5,536,233 A | 7/1996 | Khouri |
| 5,538,500 A | 7/1996 | Peterson |
| 5,540,922 A | 7/1996 | Fabo |
| 5,549,584 A | 8/1996 | Gross |
| 5,559,538 A | 9/1996 | Fleischmann |
| 5,562,107 A | 10/1996 | Lavender et al. |
| 5,579,765 A | 12/1996 | Cox et al. |
| 5,588,958 A | 12/1996 | Cunningham et al. |
| 5,603,946 A | 2/1997 | Constantine |
| 5,618,556 A | 4/1997 | Johns et al. |
| 5,624,423 A | 4/1997 | Anjur et al. |
| 5,636,643 A | 6/1997 | Argenta et al. |
| 5,637,080 A | 6/1997 | Geng |
| 5,643,189 A | 7/1997 | Masini |
| 5,645,081 A | 7/1997 | Argenta et al. |
| 5,662,599 A | 9/1997 | Reich et al. |
| 5,678,564 A | 10/1997 | Lawrence et al. |
| 5,688,225 A | 11/1997 | Walker |
| 5,701,917 A | 12/1997 | Khouri |
| 5,702,356 A | 12/1997 | Hathman |
| 5,704,905 A | 1/1998 | Jensen et al. |
| 5,713,384 A | 2/1998 | Roach et al. |
| 5,716,411 A | 2/1998 | Orgill et al. |
| 5,730,587 A | 3/1998 | Snyder et al. |
| 5,733,305 A | 3/1998 | Fleischmann |
| 5,733,337 A | 3/1998 | Carr et al. |
| 5,759,570 A * | 6/1998 | Arnold .................. 424/443 |
| 5,769,608 A | 6/1998 | Seale |
| 5,779,657 A | 7/1998 | Daneshvar |
| 5,785,688 A | 7/1998 | Joshi et al. |
| 5,795,584 A | 8/1998 | Totakura et al. |
| 5,827,213 A | 10/1998 | Jensen |
| 5,827,246 A | 10/1998 | Bowen |
| 5,830,198 A | 11/1998 | Henniges et al. |
| 5,830,496 A | 11/1998 | Freeman |
| 5,833,646 A | 11/1998 | Masini |
| 5,840,049 A | 11/1998 | Tumey et al. |
| 5,840,052 A | 11/1998 | Johns |
| 5,843,011 A | 12/1998 | Lucas |
| 5,843,025 A | 12/1998 | Shaari |
| 5,857,502 A | 1/1999 | Buchalter |
| 5,868,933 A | 2/1999 | Patrick et al. |
| 5,876,611 A | 3/1999 | Shettigar |
| 5,893,368 A | 4/1999 | Sugerman |
| 5,897,296 A | 4/1999 | Yamamoto et al. |
| 5,897,541 A | 4/1999 | Uitenbroek et al. |
| 5,911,222 A | 6/1999 | Lawrence et al. |
| 5,938,626 A | 8/1999 | Sugerman |
| 5,944,703 A | 8/1999 | Dixon et al. |
| 5,964,723 A | 10/1999 | Augustine |
| 6,010,524 A | 1/2000 | Fleischmann |
| 6,011,194 A | 1/2000 | Buglino et al. |
| 6,024,731 A | 2/2000 | Seddon et al. |
| 6,040,493 A | 3/2000 | Cooke et al. |
| 6,045,541 A | 4/2000 | Matsumoto |
| 6,068,588 A | 5/2000 | Goldowsky |
| 6,071,247 A | 6/2000 | Kennedy |
| 6,071,267 A * | 6/2000 | Zamierowski ...... A61F 13/0203 604/289 |
| 6,075,177 A | 6/2000 | Bahia et al. |
| 6,103,951 A | 8/2000 | Freeman |
| 6,110,197 A | 8/2000 | Augustine et al. |
| 6,113,548 A | 9/2000 | deBoisblanc et al. |
| 6,117,111 A | 9/2000 | Fleischmann |
| 6,117,444 A | 9/2000 | Orgill et al. |
| 6,124,520 A | 9/2000 | Roberts |
| 6,124,521 A | 9/2000 | Roberts |
| 6,135,116 A | 10/2000 | Vogel et al. |
| D434,150 S | 11/2000 | Tumey et al. |
| 6,142,982 A | 11/2000 | Hunt et al. |
| 6,156,334 A * | 12/2000 | Meyer-Ingold ......... A61L 15/32 424/443 |
| 6,168,800 B1 | 1/2001 | Dobos et al. |
| 6,174,306 B1 | 1/2001 | Fleischmann |
| 6,176,307 B1 | 1/2001 | Danos et al. |
| 6,203,563 B1 | 3/2001 | Fernandez |
| 6,225,523 B1 | 5/2001 | Masini |
| 6,231,310 B1 | 5/2001 | Tojo et al. |
| 6,249,198 B1 | 6/2001 | Clark et al. |
| 6,250,005 B1 | 6/2001 | Richards |

(56) References Cited

U.S. PATENT DOCUMENTS

| | | |
|---|---|---|
| 6,254,567 B1 | 7/2001 | Treu et al. |
| 6,255,552 B1 | 7/2001 | Cummings et al. |
| 6,261,276 B1 | 7/2001 | Reitsma |
| 6,261,283 B1 | 7/2001 | Morgan et al. |
| 6,287,521 B1 | 9/2001 | Quay et al. |
| 6,291,050 B1 | 9/2001 | Cree et al. |
| 6,297,423 B1 | 10/2001 | Schoenfeldt et al. |
| 6,323,568 B1 | 11/2001 | Zabar |
| 6,325,788 B1 | 12/2001 | McKay |
| 6,333,093 B1 | 12/2001 | Burrell et al. |
| 6,345,623 B1 | 2/2002 | Heaton et al. |
| 6,348,423 B1 | 2/2002 | Griffiths et al. |
| 6,362,390 B1 | 3/2002 | Carlucci et al. |
| 6,371,976 B1 | 4/2002 | Vrzalik |
| 6,398,767 B1 | 6/2002 | Fleischmann |
| 6,402,724 B1 | 6/2002 | Smith et al. |
| 6,406,447 B1 | 6/2002 | Thrash et al. |
| 6,413,057 B1 | 7/2002 | Hong et al. |
| 6,420,622 B1 | 7/2002 | Johnston et al. |
| 6,440,167 B2 | 8/2002 | Shimizu |
| 6,450,773 B1 | 9/2002 | Upton |
| 6,458,109 B1 | 10/2002 | Henley et al. |
| 6,465,708 B1 | 10/2002 | Augustine |
| 6,468,295 B2 | 10/2002 | Augustine et al. |
| 6,471,685 B1 | 10/2002 | Johnson |
| 6,471,982 B1 | 10/2002 | Lydon et al. |
| 6,482,491 B1 | 11/2002 | Samuelsen et al. |
| 6,488,643 B1 | 12/2002 | Tumey et al. |
| 6,491,684 B1 | 12/2002 | Joshi et al. |
| 6,500,112 B1 | 12/2002 | Khouri |
| D469,175 S | 1/2003 | Hall et al. |
| D469,176 S | 1/2003 | Hall et al. |
| 6,506,175 B1 | 1/2003 | Goldstein |
| 6,514,047 B2 | 2/2003 | Burr et al. |
| 6,520,982 B1 | 2/2003 | Boynton et al. |
| 6,528,696 B1 | 3/2003 | Ireland |
| 6,540,490 B1 | 4/2003 | Lilie |
| 6,553,998 B2 | 4/2003 | Heaton et al. |
| D475,134 S | 5/2003 | Randolph |
| 6,557,704 B1 | 5/2003 | Randolph |
| 6,566,833 B2 | 5/2003 | Bartlett |
| 6,571,825 B2 | 6/2003 | Stacy |
| 6,586,653 B2 | 7/2003 | Graeme, III et al. |
| 6,589,028 B1 | 7/2003 | Eckerbom et al. |
| 6,595,949 B1 | 7/2003 | Shapiro |
| 6,599,262 B1 | 7/2003 | Masini |
| D478,659 S | 8/2003 | Hall et al. |
| 6,604,908 B1 | 8/2003 | Bryant et al. |
| 6,607,495 B1 | 8/2003 | Skalak et al. |
| 6,613,953 B1 | 9/2003 | Altura |
| 6,618,221 B2 | 9/2003 | Gillis et al. |
| 6,623,255 B2 | 9/2003 | Joong et al. |
| 6,626,891 B2 | 9/2003 | Ohmstede |
| 6,638,035 B1 | 10/2003 | Puff |
| 6,648,862 B2 | 11/2003 | Watson |
| 6,673,028 B1 | 1/2004 | Argenta et al. |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,706,940 B2 | 3/2004 | Worthley |
| D488,558 S | 4/2004 | Hall |
| 6,719,742 B1 | 4/2004 | McCormack et al. |
| 6,752,794 B2 | 6/2004 | Lockwood et al. |
| 6,755,807 B2 | 6/2004 | Risk, Jr. et al. |
| 6,762,337 B2 | 7/2004 | Boukanov et al. |
| 6,764,459 B1 | 7/2004 | Donaldson |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,887,228 B2 | 5/2005 | McKay |
| 6,887,263 B2 | 5/2005 | Bleam et al. |
| 6,904,631 B2 | 6/2005 | Vrzalik et al. |
| 6,936,037 B2 | 8/2005 | Bubb |
| 6,942,633 B2 | 9/2005 | Odland |
| 6,942,634 B2 | 9/2005 | Odland |
| 6,951,553 B2 | 10/2005 | Bubb et al. |
| 6,960,179 B2 | 11/2005 | Gura |
| 6,960,181 B2 | 11/2005 | Stevens |
| 6,966,901 B2 | 11/2005 | Leisner et al. |
| 6,977,323 B1 | 12/2005 | Swenson |
| 6,979,324 B2 | 12/2005 | Bybordi et al. |
| 6,988,423 B2 | 1/2006 | Bolam et al. |
| 6,994,702 B1 | 2/2006 | Johnson |
| 6,998,511 B2 | 2/2006 | Worthley |
| 7,004,915 B2 | 2/2006 | Boynton et al. |
| 7,022,113 B2 | 4/2006 | Lockwood et al. |
| 7,037,254 B2 | 5/2006 | O'Connor et al. |
| 7,048,706 B2 | 5/2006 | Cea |
| 7,049,478 B1 | 5/2006 | Smith et al. |
| 7,052,167 B2 | 5/2006 | Vanderschuit |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,087,807 B2 | 8/2006 | Stapf |
| 7,108,683 B2 | 9/2006 | Zamierowski |
| 7,117,869 B2 | 10/2006 | Heaton et al. |
| 7,118,545 B2 | 10/2006 | Boyde |
| 7,128,719 B2 | 10/2006 | Rosenberg |
| 7,128,735 B2 | 10/2006 | Weston |
| 7,144,390 B1 | 12/2006 | Hannigan et al. |
| 7,151,348 B1 | 12/2006 | Ueda et al. |
| 7,169,151 B1 | 1/2007 | Lytinas |
| 7,182,085 B1 | 2/2007 | Larsen et al. |
| 7,182,758 B2 | 2/2007 | McCraw |
| 7,195,624 B2 | 3/2007 | Lockwood |
| 7,198,046 B1 | 4/2007 | Argenta et al. |
| 7,214,202 B1 | 5/2007 | Vogel et al. |
| 7,216,651 B2 | 5/2007 | Argenta et al. |
| D544,092 S | 6/2007 | Lewis |
| 7,238,850 B2 | 7/2007 | Shimanuki |
| 7,273,054 B2 | 9/2007 | Heaton et al. |
| 7,276,051 B1 | 10/2007 | Henley et al. |
| 7,279,612 B1 | 10/2007 | Heaton et al. |
| 7,294,751 B2 | 11/2007 | Propp et al. |
| 7,294,752 B1 | 11/2007 | Propp |
| 7,316,672 B1 | 1/2008 | Hunt et al. |
| 7,322,971 B2 | 1/2008 | Shehada |
| 7,335,809 B2 | 2/2008 | Riesinger |
| D565,177 S | 3/2008 | Locke et al. |
| 7,338,482 B2 | 3/2008 | Lockwood et al. |
| 7,351,250 B2 | 4/2008 | Zamierowski |
| 7,361,184 B2 * | 4/2008 | Joshi .............................. 606/213 |
| 7,374,409 B2 | 5/2008 | Kawamura |
| 7,381,211 B2 | 6/2008 | Zamierowski |
| 7,381,859 B2 | 6/2008 | Hunt et al. |
| 7,396,345 B2 | 7/2008 | Knighton et al. |
| 7,401,703 B2 | 7/2008 | McMichael et al. |
| 7,410,495 B2 | 8/2008 | Zamierowski |
| 7,413,570 B2 | 8/2008 | Zamierowski |
| 7,413,571 B2 | 8/2008 | Zamierowski |
| 7,422,576 B2 | 9/2008 | Boynton et al. |
| 7,429,689 B2 | 9/2008 | Chen et al. |
| 7,438,705 B2 | 10/2008 | Karpowicz et al. |
| 7,476,205 B2 | 1/2009 | Erdmann |
| 7,485,112 B2 | 2/2009 | Karpowicz et al. |
| 7,494,482 B2 | 2/2009 | Orgill et al. |
| 7,503,910 B2 | 3/2009 | Adahan |
| 7,511,187 B2 | 3/2009 | Kelly |
| 7,524,315 B2 | 4/2009 | Blott et al. |
| 7,534,240 B1 | 5/2009 | Johnson |
| 7,534,927 B2 | 5/2009 | Lockwood |
| 7,553,306 B1 | 6/2009 | Hunt et al. |
| 7,563,940 B2 | 7/2009 | Kurata |
| 7,569,742 B2 | 8/2009 | Haggstrom et al. |
| 7,576,256 B2 | 8/2009 | Björnberg et al. |
| 7,601,129 B2 | 10/2009 | Aali |
| 7,605,298 B2 | 10/2009 | Bechert et al. |

(56) References Cited

U.S. PATENT DOCUMENTS

| | | |
|---|---|---|
| 7,611,500 B1 | 11/2009 | Lina et al. |
| 7,612,247 B2 | 11/2009 | Oyaski |
| 7,615,036 B2 | 11/2009 | Joshi et al. |
| 7,622,629 B2 | 11/2009 | Aali |
| 7,645,253 B2 * | 1/2010 | Gura ............... A61M 1/16 210/645 |
| 7,645,269 B2 | 1/2010 | Zamierowski |
| 7,678,090 B2 | 3/2010 | Risk, Jr. et al. |
| 7,678,102 B1 | 3/2010 | Heaton |
| 7,699,823 B2 | 4/2010 | Haggstrom et al. |
| 7,699,830 B2 | 4/2010 | Martin |
| 7,708,724 B2 | 5/2010 | Weston |
| 7,717,313 B2 | 5/2010 | Criscuolo et al. |
| 7,722,582 B2 | 5/2010 | Lina et al. |
| 7,723,561 B2 | 5/2010 | Propp |
| 7,745,681 B1 | 6/2010 | Ferguson |
| 7,749,531 B2 | 7/2010 | Booher |
| 7,753,894 B2 | 7/2010 | Blott et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,785,247 B2 | 8/2010 | Tatum et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,815,616 B2 | 10/2010 | Boehringer et al. |
| 7,816,577 B2 | 10/2010 | Aali |
| 7,825,289 B2 | 11/2010 | Vess |
| 7,828,782 B2 | 11/2010 | Suzuki |
| 7,838,716 B2 | 11/2010 | de Luis et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,858,838 B2 | 12/2010 | Holm et al. |
| 7,862,339 B2 | 1/2011 | Mulligan |
| 7,880,050 B2 | 2/2011 | Robinson et al. |
| 7,883,494 B2 | 2/2011 | Martin |
| 7,884,258 B2 | 2/2011 | Boehringer et al. |
| 7,896,823 B2 | 3/2011 | Mangrum et al. |
| 7,896,856 B2 | 3/2011 | Petrosenko et al. |
| 7,909,805 B2 | 3/2011 | Weston |
| 7,910,791 B2 * | 3/2011 | Coffey ............... A61F 13/02 424/443 |
| 7,922,703 B2 | 4/2011 | Riesinger |
| 7,931,630 B2 | 4/2011 | Nishtala et al. |
| 7,935,066 B2 | 5/2011 | Shives et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,988,673 B2 | 8/2011 | Wright et al. |
| 7,998,125 B2 | 8/2011 | Weston |
| 8,007,257 B2 | 8/2011 | Heaton et al. |
| 8,021,347 B2 | 9/2011 | Vitaris et al. |
| 8,025,650 B2 | 9/2011 | Anderson et al. |
| 8,034,038 B2 | 10/2011 | Biggie et al. |
| 8,062,272 B2 | 11/2011 | Weston |
| 8,062,273 B2 | 11/2011 | Weston |
| 8,080,702 B2 | 12/2011 | Blott et al. |
| 8,092,436 B2 | 1/2012 | Christensen |
| 8,100,887 B2 | 1/2012 | Weston |
| 8,105,295 B2 | 1/2012 | Blott et al. |
| 8,118,794 B2 | 2/2012 | Weston |
| 8,128,615 B2 | 3/2012 | Blott |
| 8,152,785 B2 | 4/2012 | Vitaris |
| 8,158,844 B2 | 4/2012 | McNeil |
| 8,162,907 B2 | 4/2012 | Heagle |
| 8,162,909 B2 | 4/2012 | Blott et al. |
| 8,167,869 B2 | 5/2012 | Wudyka |
| 8,186,978 B2 | 5/2012 | Tinholt et al. |
| 8,211,071 B2 | 7/2012 | Mormino et al. |
| 8,212,101 B2 | 7/2012 | Propp |
| 8,215,929 B2 | 7/2012 | Shen et al. |
| 8,235,955 B2 | 8/2012 | Blott et al. |
| 8,241,261 B2 | 8/2012 | Randolph et al. |
| 8,251,979 B2 | 8/2012 | Malhi |
| 8,252,971 B2 | 8/2012 | Aali et al. |
| 8,257,327 B2 | 9/2012 | Blott et al. |
| 8,257,328 B2 | 9/2012 | Augustine et al. |
| 8,267,908 B2 | 9/2012 | Coulthard |
| 8,282,611 B2 | 10/2012 | Weston |
| 8,303,552 B2 | 11/2012 | Weston |
| 8,308,714 B2 | 11/2012 | Weston et al. |
| 8,314,283 B2 | 11/2012 | Kingsford et al. |
| 8,323,264 B2 | 12/2012 | Weston et al. |
| 8,328,858 B2 | 12/2012 | Barsky et al. |
| 8,382,731 B2 | 2/2013 | Johannison |
| 8,403,899 B2 | 3/2013 | Sherman |
| 8,404,921 B2 | 3/2013 | Lee et al. |
| D679,819 S | 4/2013 | Peron |
| D679,820 S | 4/2013 | Peron |
| 8,449,509 B2 | 5/2013 | Weston |
| 2001/0001278 A1 | 5/2001 | Drevet |
| 2001/0029956 A1 | 10/2001 | Argenta |
| 2001/0031943 A1 | 10/2001 | Urie |
| 2001/0033795 A1 | 10/2001 | Humphries |
| 2001/0034499 A1 | 10/2001 | Sessions et al. |
| 2001/0043870 A1 | 11/2001 | Song |
| 2001/0043943 A1 | 11/2001 | Coffey |
| 2001/0051178 A1 | 12/2001 | Blatchford et al. |
| 2002/0002209 A1 | 1/2002 | Mork |
| 2002/0016577 A1 | 2/2002 | Ohmstede |
| 2002/0019602 A1 | 2/2002 | Geng |
| 2002/0040687 A1 | 4/2002 | van Der Lely et al. |
| 2002/0065494 A1 | 5/2002 | Lockwood et al. |
| 2002/0068913 A1 | 6/2002 | Fleischmann |
| 2002/0110672 A1 | 8/2002 | Muratore-Pallatino et al. |
| 2002/0115952 A1 | 8/2002 | Tumey |
| 2002/0120185 A1 | 8/2002 | Johnson |
| 2002/0122732 A1 | 9/2002 | Oh et al. |
| 2002/0143286 A1 | 10/2002 | Tumey |
| 2002/0150720 A1 | 10/2002 | Howard et al. |
| 2002/0151836 A1 | 10/2002 | Burden |
| 2002/0161346 A1 | 10/2002 | Lockwood et al. |
| 2002/0164255 A1 | 11/2002 | Burr et al. |
| 2002/0169405 A1 | 11/2002 | Roberts |
| 2002/0183702 A1 | 12/2002 | Henley et al. |
| 2002/0198503 A1 | 12/2002 | Risk et al. |
| 2002/0198504 A1 | 12/2002 | Risk et al. |
| 2003/0009122 A1 | 1/2003 | Veras |
| 2003/0014022 A1 | 1/2003 | Lockwood et al. |
| 2003/0014025 A1 | 1/2003 | Allen et al. |
| 2003/0021775 A1 | 1/2003 | Freeman |
| 2003/0035743 A1 | 2/2003 | Lee et al. |
| 2003/0040687 A1 * | 2/2003 | Boynton ............... A61M 1/0031 601/6 |
| 2003/0045825 A1 | 3/2003 | Etheredge, III |
| 2003/0050594 A1 | 3/2003 | Zamierowski |
| 2003/0069563 A1 | 4/2003 | Johnson |
| 2003/0078532 A1 | 4/2003 | Ruszczak et al. |
| 2003/0088202 A1 | 5/2003 | Gilman |
| 2003/0093041 A1 | 5/2003 | Risk, Jr. et al. |
| 2003/0095879 A1 | 5/2003 | Oh et al. |
| 2003/0099558 A1 | 5/2003 | Chang |
| 2003/0108430 A1 | 6/2003 | Yoshida et al. |
| 2003/0108587 A1 | 6/2003 | Orgill et al. |
| 2003/0114818 A1 | 6/2003 | Benecke et al. |
| 2003/0125646 A1 | 7/2003 | Whitlock |
| 2003/0125649 A1 | 7/2003 | Mcintosh et al. |
| 2003/0133812 A1 | 7/2003 | Puff et al. |
| 2003/0144619 A1 | 7/2003 | Augustine |
| 2003/0162071 A1 | 8/2003 | Yasuda |
| 2003/0171675 A1 | 9/2003 | Rosenberg |
| 2003/0175125 A1 | 9/2003 | Kwon et al. |
| 2003/0175135 A1 | 9/2003 | Heo et al. |
| 2003/0175798 A1 | 9/2003 | Raees et al. |
| 2003/0180341 A1 | 9/2003 | Gooch et al. |
| 2003/0199800 A1 | 10/2003 | Levin |

(56) References Cited

U.S. PATENT DOCUMENTS

| | | |
|---|---|---|
| 2003/0208149 A1 | 11/2003 | Coffey |
| 2003/0212357 A1 | 11/2003 | Pace |
| 2003/0212359 A1 | 11/2003 | Butler |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2004/0001878 A1* | 1/2004 | DeBusk et al. ............... 424/445 |
| 2004/0005222 A1 | 1/2004 | Yoshida et al. |
| 2004/0006319 A1 | 1/2004 | Lina et al. |
| 2004/0019252 A1* | 1/2004 | Hirata ......................... 600/114 |
| 2004/0019342 A1 | 1/2004 | Nagasuna et al. |
| 2004/0021123 A1 | 2/2004 | Howell et al. |
| 2004/0030304 A1 | 2/2004 | Hunt et al. |
| 2004/0039391 A1 | 2/2004 | Argenta et al. |
| 2004/0039415 A1 | 2/2004 | Zamierowski |
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0066097 A1 | 4/2004 | Kobayashi et al. |
| 2004/0071568 A1 | 4/2004 | Hyeon |
| 2004/0073151 A1 | 4/2004 | Weston |
| 2004/0078011 A1 | 4/2004 | Stevens |
| 2004/0093026 A1 | 5/2004 | Weidenhagen et al. |
| 2004/0106888 A1 | 6/2004 | Lutri et al. |
| 2004/0115076 A1 | 6/2004 | Lilie et al. |
| 2004/0122434 A1 | 6/2004 | Argenta et al. |
| 2004/0126250 A1 | 7/2004 | Tsuchiya et al. |
| 2004/0127834 A1 | 7/2004 | Sigurjonsson et al. |
| 2004/0127862 A1 | 7/2004 | Bubb et al. |
| 2004/0127863 A1 | 7/2004 | Bubb et al. |
| 2004/0138602 A1 | 7/2004 | Rossen |
| 2004/0156730 A1 | 8/2004 | Lilie et al. |
| 2004/0162512 A1 | 8/2004 | Liedtke et al. |
| 2004/0167482 A1 | 8/2004 | Watson |
| 2004/0189103 A1 | 9/2004 | Duncan et al. |
| 2004/0193218 A1 | 9/2004 | Butler |
| 2004/0225208 A1 | 11/2004 | Johnson |
| 2004/0241213 A1 | 12/2004 | Bray |
| 2004/0241214 A1* | 12/2004 | Kirkwood ............ A61F 13/0213 424/445 |
| 2004/0243042 A1 | 12/2004 | Lipman |
| 2004/0243073 A1 | 12/2004 | Lockwood et al. |
| 2004/0249353 A1 | 12/2004 | Risk, Jr. et al. |
| 2004/0260230 A1 | 12/2004 | Randolph |
| 2005/0004534 A1 | 1/2005 | Lockwood et al. |
| 2005/0010153 A1 | 1/2005 | Lockwood et al. |
| 2005/0015036 A1 | 1/2005 | Lutri et al. |
| 2005/0020955 A1 | 1/2005 | Sanders et al. |
| 2005/0028828 A1 | 2/2005 | Heaton et al. |
| 2005/0031470 A1 | 2/2005 | Lee |
| 2005/0058694 A1 | 3/2005 | Nielsen |
| 2005/0070835 A1 | 3/2005 | Joshi |
| 2005/0070858 A1 | 3/2005 | Lockwood et al. |
| 2005/0080372 A1 | 4/2005 | Nielsen et al. |
| 2005/0085795 A1 | 4/2005 | Lockwood et al. |
| 2005/0090787 A1 | 4/2005 | Risk, Jr. et al. |
| 2005/0098031 A1 | 5/2005 | Yoon et al. |
| 2005/0100450 A1 | 5/2005 | Bryant et al. |
| 2005/0111987 A1 | 5/2005 | Yoo et al. |
| 2005/0119737 A1 | 6/2005 | Bene et al. |
| 2005/0123422 A1 | 6/2005 | Lilie |
| 2005/0129540 A1 | 6/2005 | Puff |
| 2005/0131327 A1 | 6/2005 | Lockwood et al. |
| 2005/0135946 A1 | 6/2005 | Kang et al. |
| 2005/0137539 A1 | 6/2005 | Biggie et al. |
| 2005/0142007 A1 | 6/2005 | Lee et al. |
| 2005/0142008 A1 | 6/2005 | Jung et al. |
| 2005/0147562 A1 | 7/2005 | Hunter et al. |
| 2005/0148913 A1 | 7/2005 | Weston |
| 2005/0163635 A1 | 7/2005 | Berwanger et al. |
| 2005/0177086 A1 | 8/2005 | Murata et al. |
| 2005/0177190 A1 | 8/2005 | Zamierowski |
| 2005/0182445 A1 | 8/2005 | Zamierowski |
| 2005/0222527 A1 | 10/2005 | Miller et al. |
| 2005/0222544 A1 | 10/2005 | Weston |
| 2005/0261642 A1* | 11/2005 | Weston ............... A61M 1/0031 604/313 |
| 2005/0261643 A1 | 11/2005 | Bybordi et al. |
| 2005/0271526 A1 | 12/2005 | Chang et al. |
| 2005/0276706 A1 | 12/2005 | Radue |
| 2006/0009744 A1 | 1/2006 | Erdman et al. |
| 2006/0015087 A1 | 1/2006 | Risk, Jr. et al. |
| 2006/0017332 A1 | 1/2006 | Kang et al. |
| 2006/0018771 A1 | 1/2006 | Song et al. |
| 2006/0020234 A1 | 1/2006 | Chou et al. |
| 2006/0024181 A1 | 2/2006 | Kim |
| 2006/0025727 A1 | 2/2006 | Boehringer et al. |
| 2006/0029650 A1 | 2/2006 | Coffey |
| 2006/0039742 A1 | 2/2006 | Cable, Jr. et al. |
| 2006/0041247 A1 | 2/2006 | Petrosenko et al. |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0069365 A1 | 3/2006 | Sperl et al. |
| 2006/0070458 A1 | 4/2006 | Jones et al. |
| 2006/0079852 A1 | 4/2006 | Bubb et al. |
| 2006/0100586 A1 | 5/2006 | Karpowicz et al. |
| 2006/0100594 A1 | 5/2006 | Adams et al. |
| 2006/0100597 A1 | 5/2006 | Miskie |
| 2006/0110259 A1 | 5/2006 | Puff et al. |
| 2006/0116620 A1 | 6/2006 | Oyaski |
| 2006/0122548 A1 | 6/2006 | Abrams |
| 2006/0149170 A1 | 7/2006 | Boynton et al. |
| 2006/0206047 A1 | 9/2006 | Lampe et al. |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0251523 A1 | 11/2006 | Lee et al. |
| 2006/0271020 A1 | 11/2006 | Huang et al. |
| 2007/0003604 A1 | 1/2007 | Jones et al. |
| 2007/0005028 A1 | 1/2007 | Risk, Jr. et al. |
| 2007/0014837 A1 | 1/2007 | Johnson et al. |
| 2007/0016152 A1 | 1/2007 | Karpowicz |
| 2007/0021697 A1 | 1/2007 | Ginther et al. |
| 2007/0027414 A1 | 2/2007 | Hoffman et al. |
| 2007/0032754 A1 | 2/2007 | Walsh |
| 2007/0032755 A1 | 2/2007 | Walsh |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0041856 A1 | 2/2007 | Hansen et al. |
| 2007/0052144 A1 | 3/2007 | Knirck et al. |
| 2007/0055209 A1 | 3/2007 | Patel et al. |
| 2007/0066946 A1 | 3/2007 | Haggstrom et al. |
| 2007/0078366 A1 | 4/2007 | Haggstrom et al. |
| 2007/0078467 A1 | 4/2007 | Mullen |
| 2007/0100308 A1 | 5/2007 | Miyairi |
| 2007/0141128 A1 | 6/2007 | Blott et al. |
| 2007/0167927 A1 | 7/2007 | Hunt et al. |
| 2007/0179460 A1 | 8/2007 | Adahan |
| 2007/0185426 A1 | 8/2007 | Ambrosio et al. |
| 2007/0185463 A1 | 8/2007 | Mulligan |
| 2007/0196214 A1 | 8/2007 | Bocchiola |
| 2007/0219532 A1 | 9/2007 | Karpowicz et al. |
| 2007/0225663 A1 | 9/2007 | Watt et al. |
| 2007/0256428 A1 | 11/2007 | Unger et al. |
| 2007/0260207 A1 | 11/2007 | Ugander et al. |
| 2007/0265585 A1 | 11/2007 | Joshi et al. |
| 2007/0265586 A1 | 11/2007 | Joshi et al. |
| 2007/0282236 A1 | 12/2007 | LaGreca |
| 2007/0292286 A1 | 12/2007 | Hell et al. |
| 2007/0295201 A1 | 12/2007 | Dadd |
| 2008/0008607 A1 | 1/2008 | Schade et al. |
| 2008/0009812 A1 | 1/2008 | Riesinger |
| 2008/0058691 A1 | 3/2008 | Sorensen |
| 2008/0071235 A1 | 3/2008 | Locke |
| 2008/0082059 A1 | 4/2008 | Fink et al. |
| 2008/0089796 A1 | 4/2008 | Schade et al. |
| 2008/0119802 A1 | 5/2008 | Riesinger |
| 2008/0167592 A1 | 7/2008 | Greer |
| 2008/0167593 A1 | 7/2008 | Fleischmann |
| 2008/0183119 A1 | 7/2008 | Joshi |

(56) References Cited

U.S. PATENT DOCUMENTS

| | | |
|---|---|---|
| 2008/0188820 A1 | 8/2008 | Joshi |
| 2008/0191399 A1 | 8/2008 | Chang |
| 2008/0200857 A1 | 8/2008 | Lawhorn |
| 2008/0200906 A1 | 8/2008 | Sanders et al. |
| 2008/0208147 A1 | 8/2008 | Argenta et al. |
| 2008/0211435 A1 | 9/2008 | Imagawa |
| 2008/0223378 A1 | 9/2008 | Henderson et al. |
| 2008/0234641 A1 | 9/2008 | Locke et al. |
| 2008/0240942 A1 | 10/2008 | Heinrich et al. |
| 2008/0267797 A1 | 10/2008 | Hell et al. |
| 2008/0294147 A1 | 11/2008 | Radl et al. |
| 2008/0306407 A1 | 12/2008 | Taylor |
| 2008/0306456 A1 | 12/2008 | Riesinger |
| 2008/0312572 A1 | 12/2008 | Riesinger |
| 2009/0005746 A1 | 1/2009 | Nielsen et al. |
| 2009/0012441 A1 | 1/2009 | Mulligan |
| 2009/0030383 A1 | 1/2009 | Larsen et al. |
| 2009/0036873 A1 | 2/2009 | Nielsen et al. |
| 2009/0054855 A1 | 2/2009 | Blott et al. |
| 2009/0060750 A1 | 3/2009 | Chen et al. |
| 2009/0069759 A1 | 3/2009 | Blott et al. |
| 2009/0081049 A1 | 3/2009 | Tian et al. |
| 2009/0082740 A1 | 3/2009 | Lockwood et al. |
| 2009/0087323 A1 | 4/2009 | Blakey et al. |
| 2009/0124988 A1 | 5/2009 | Coulthard |
| 2009/0125004 A1 | 5/2009 | Shen et al. |
| 2009/0129955 A1 | 5/2009 | Schubert |
| 2009/0131888 A1 | 5/2009 | Joshi |
| 2009/0131892 A1 | 5/2009 | Karpowicz et al. |
| 2009/0137973 A1 | 5/2009 | Karpowicz et al. |
| 2009/0148320 A1 | 6/2009 | Lucas |
| 2009/0169402 A1 | 7/2009 | Stenberg |
| 2009/0192499 A1 | 7/2009 | Weston et al. |
| 2009/0198201 A1 | 8/2009 | Adahan |
| 2009/0204085 A1 | 8/2009 | Biggie et al. |
| 2009/0206778 A1 | 8/2009 | Roh et al. |
| 2009/0216170 A1 | 8/2009 | Robinson et al. |
| 2009/0221977 A1 | 9/2009 | Blott et al. |
| 2009/0227935 A1 | 9/2009 | Zanella et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254053 A1 | 10/2009 | Svensby et al. |
| 2009/0254054 A1 | 10/2009 | Blott et al. |
| 2009/0264837 A1 | 10/2009 | Adahan |
| 2009/0270820 A1 | 10/2009 | Johnson et al. |
| 2009/0280015 A1 | 11/2009 | Lillie et al. |
| 2009/0292263 A1 | 11/2009 | Hudspeth et al. |
| 2009/0292264 A1 | 11/2009 | Hudspeth et al. |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299308 A1 | 12/2009 | Kazala et al. |
| 2009/0299340 A1 | 12/2009 | Kazala et al. |
| 2009/0299341 A1 | 12/2009 | Kazala, Jr. et al. |
| 2009/0299342 A1 | 12/2009 | Cavanaugh, II et al. |
| 2009/0304534 A1 | 12/2009 | Richter |
| 2009/0306580 A1 | 12/2009 | Blott et al. |
| 2009/0312723 A1 | 12/2009 | Blott et al. |
| 2009/0312725 A1 | 12/2009 | Braga |
| 2009/0312728 A1 | 12/2009 | Randolph et al. |
| 2009/0326487 A1 | 12/2009 | Vitaris |
| 2010/0004611 A1 | 1/2010 | Aali |
| 2010/0016767 A1 | 1/2010 | Jones et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036334 A1 | 2/2010 | Heagle et al. |
| 2010/0036367 A1 | 2/2010 | Krohn |
| 2010/0055158 A1 | 3/2010 | Vitaris et al. |
| 2010/0063483 A1 | 3/2010 | Adahan |
| 2010/0063484 A1 | 3/2010 | Heagle |
| 2010/0069858 A1 | 3/2010 | Olson |
| 2010/0069863 A1 | 3/2010 | Olson |
| 2010/0084074 A1 | 4/2010 | McClernon et al. |
| 2010/0087767 A1 | 4/2010 | McNeil |
| 2010/0098566 A1 | 4/2010 | Kang |
| 2010/0100063 A1 | 4/2010 | Joshi et al. |
| 2010/0106112 A1 | 4/2010 | Vogel |
| 2010/0106114 A1 | 4/2010 | Weston et al. |
| 2010/0106120 A1 | 4/2010 | Holm |
| 2010/0106121 A1 | 4/2010 | Holm |
| 2010/0121286 A1 | 5/2010 | Locke et al. |
| 2010/0122417 A1 | 5/2010 | Vrzalik et al. |
| 2010/0125234 A1 | 5/2010 | Smith |
| 2010/0125258 A1 | 5/2010 | Coulthard et al. |
| 2010/0150991 A1 | 6/2010 | Bernstein |
| 2010/0159192 A1 | 6/2010 | Cotton |
| 2010/0160879 A1 | 6/2010 | Weston |
| 2010/0160880 A1 | 6/2010 | Weston |
| 2010/0160881 A1 | 6/2010 | Lin et al. |
| 2010/0174251 A1 | 7/2010 | Weston |
| 2010/0191196 A1 | 7/2010 | Heagle |
| 2010/0191198 A1 | 7/2010 | Heagle |
| 2010/0207768 A1 | 8/2010 | Pidgeon |
| 2010/0210986 A1 | 8/2010 | Sanders |
| 2010/0217177 A1 | 8/2010 | Cali et al. |
| 2010/0249733 A9 | 9/2010 | Blott et al. |
| 2010/0262090 A1 | 10/2010 | Riesinger |
| 2010/0262091 A1 | 10/2010 | Larsson |
| 2010/0268198 A1 | 10/2010 | Buan et al. |
| 2010/0274207 A1 | 10/2010 | Weston |
| 2010/0280468 A1 | 11/2010 | Haggstrom et al. |
| 2010/0286635 A1 | 11/2010 | Watson, Jr. |
| 2010/0298866 A1 | 11/2010 | Fischvogt |
| 2010/0305490 A1 | 12/2010 | Coulthard et al. |
| 2010/0305524 A1 | 12/2010 | Vess et al. |
| 2010/0305526 A1 | 12/2010 | Robinson et al. |
| 2010/0318043 A1 | 12/2010 | Malhi et al. |
| 2010/0318052 A1 | 12/2010 | Ha et al. |
| 2010/0320659 A1 | 12/2010 | Chen et al. |
| 2010/0324510 A1 | 12/2010 | Andresen et al. |
| 2010/0324516 A1 | 12/2010 | Braga et al. |
| 2010/0331797 A1 | 12/2010 | Patet et al. |
| 2011/0004172 A1 | 1/2011 | Eckstein et al. |
| 2011/0009835 A1 | 1/2011 | Blott |
| 2011/0015593 A1 | 1/2011 | Svedman et al. |
| 2011/0028290 A1 | 2/2011 | Ozawa |
| 2011/0028918 A1 | 2/2011 | Hartwell |
| 2011/0028919 A1 | 2/2011 | Johnnison et al. |
| 2011/0028921 A1 | 2/2011 | Hartwell et al. |
| 2011/0034888 A1 | 2/2011 | Aali |
| 2011/0034892 A1 | 2/2011 | Buan |
| 2011/0043055 A1 | 2/2011 | Chiang |
| 2011/0046584 A1 | 2/2011 | Haggstrom et al. |
| 2011/0046585 A1 | 2/2011 | Weston |
| 2011/0052664 A1 | 3/2011 | Tennican et al. |
| 2011/0054421 A1 | 3/2011 | Hartwell |
| 2011/0054422 A1 | 3/2011 | Locke et al. |
| 2011/0054423 A1 | 3/2011 | Blott et al. |
| 2011/0081267 A1 | 4/2011 | McCrone et al. |
| 2011/0087176 A2 | 4/2011 | Blott |
| 2011/0087178 A2 | 4/2011 | Weston |
| 2011/0087180 A2 | 4/2011 | Weston |
| 2011/0092927 A1 | 4/2011 | Wilkes et al. |
| 2011/0092958 A1 | 4/2011 | Jacobs |
| 2011/0098621 A1 | 4/2011 | Fabo et al. |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0125066 A1 | 5/2011 | Robinson et al. |
| 2011/0130712 A1 | 6/2011 | Topaz |
| 2011/0137222 A1 | 6/2011 | Masini |
| 2011/0169348 A1 | 7/2011 | Park |

(56) References Cited

U.S. PATENT DOCUMENTS

| | | | |
|---|---|---|---|
| 2011/0172615 A2 | 7/2011 | Greener et al. |
| 2011/0172617 A1 | 7/2011 | Riesinger |
| 2011/0176946 A1 | 7/2011 | Drevet |
| 2011/0178375 A1 | 7/2011 | Forster |
| 2011/0186765 A1 | 8/2011 | Jaeb et al. |
| 2011/0205646 A1 | 8/2011 | Sato et al. |
| 2011/0205647 A1 | 8/2011 | Osaka et al. |
| 2011/0218509 A1 | 9/2011 | Dontas |
| 2011/0230849 A1 | 9/2011 | Coulthard et al. |
| 2011/0237863 A1 | 9/2011 | Ricci et al. |
| 2011/0245788 A1 | 10/2011 | Marquez Canada |
| 2011/0247636 A1 | 10/2011 | Pollack |
| 2011/0251567 A1 | 10/2011 | Blott et al. |
| 2011/0257572 A1 | 10/2011 | Locke et al. |
| 2011/0275964 A1 | 11/2011 | Greener |
| 2011/0282309 A1 | 11/2011 | Adie et al. |
| 2012/0041403 A1 | 2/2012 | Bennett et al. |
| 2012/0053538 A1 | 3/2012 | Blott et al. |
| 2012/0065664 A1 | 3/2012 | Avitable et al. |
| 2012/0095380 A1 | 4/2012 | Gergely et al. |
| 2012/0095426 A1 | 4/2012 | Visscher et al. |
| 2012/0101465 A1 | 4/2012 | Mcguire, Jr. |
| 2012/0109084 A1 | 5/2012 | Blott et al. |
| 2012/0123311 A1 | 5/2012 | Weidemann-Hendrickson et al. |
| 2012/0136325 A1 | 5/2012 | Allen |
| 2012/0157942 A1 | 6/2012 | Weston |
| 2012/0160091 A1 | 6/2012 | Dadd et al. |
| 2012/0165764 A1 | 6/2012 | Allen et al. |
| 2012/0172778 A1 | 7/2012 | Rastegar et al. |
| 2012/0177513 A1 | 7/2012 | Lilie et al. |
| 2012/0203145 A1 | 8/2012 | Nilsson |
| 2012/0203189 A1 | 8/2012 | Barta et al. |
| 2012/0209224 A1 | 8/2012 | Weston |
| 2012/0232502 A1 | 9/2012 | Lowing |
| 2012/0238932 A1 | 9/2012 | Atteia et al. |
| 2012/0251359 A1 | 10/2012 | Neelakantan et al. |
| 2014/0018753 A1 | 1/2014 | Joshi et al. |
| 2014/0031771 A1 | 1/2014 | Locke et al. |
| 2014/0039423 A1 | 2/2014 | Reisinger |

FOREIGN PATENT DOCUMENTS

| | | |
|---|---|---|
| CA | 2414393 A1 | 11/1992 |
| CA | 2198243 A1 | 2/1996 |
| CA | 2238413 A1 | 5/1997 |
| CA | 2471780 A1 | 3/1999 |
| CA | 2367460 A1 | 10/2000 |
| CA | 2390513 A1 | 5/2001 |
| CA | 2121688 C | 7/2001 |
| CA | 2408305 A1 | 11/2001 |
| CA | 2432293 A1 | 2/2003 |
| CA | 2458285 A1 | 3/2003 |
| CA | 2157772 C | 9/2003 |
| DE | 33446 C | 10/1885 |
| DE | 561757 C | 10/1932 |
| DE | 847475 A | 8/1952 |
| DE | 2809828 | 9/1978 |
| DE | 3 032 092 A1 | 4/1982 |
| DE | 3 137 839 A1 | 3/1983 |
| DE | 3 935 818 | 5/1991 |
| DE | 4 012 232 | 10/1991 |
| DE | 90 17 289 U1 | 6/1992 |
| DE | 4 111 122 A1 | 4/1993 |
| DE | 3850798 T2 | 2/1995 |
| DE | 295 04 378 U1 | 10/1995 |
| DE | 195 17 699 A1 | 11/1996 |
| DE | 198 44 355 | 4/2000 |
| DE | 10059439 A1 | 8/2001 |
| EP | 0 020 662 | 7/1984 |
| EP | 0298726 * | 1/1989 |
| EP | 0298726 B1 | 1/1989 |
| EP | 0 355 186 | 2/1990 |
| EP | 0358302 A2 | 3/1990 |
| EP | 0 541 251 A1 | 5/1993 |
| EP | 0 617 152 A1 | 9/1994 |
| EP | 0 619 105 A1 | 10/1994 |
| EP | 0 793 019 A2 | 9/1997 |
| EP | 0762860 B1 | 12/1997 |
| EP | 0 777 504 | 10/1998 |
| EP | 0 782 421 | 7/1999 |
| EP | 0 941 726 A1 | 9/1999 |
| EP | 1 068 451 A1 | 10/1999 |
| EP | 1 013 290 A1 | 6/2000 |
| EP | 1088589 A2 | 4/2001 |
| EP | 1 411 874 A1 | 7/2001 |
| EP | 1129734 A2 | 9/2001 |
| EP | 1 283 702 A1 | 11/2001 |
| EP | 1177781 A2 | 2/2002 |
| EP | 1 339 366 A2 | 6/2002 |
| EP | 1219311 B1 | 7/2002 |
| EP | 1 897 569 | 8/2002 |
| EP | 0853950 B1 | 10/2002 |
| EP | 0 708 620 | 5/2003 |
| EP | 1 088 569 | 8/2003 |
| EP | 1 440 667 | 3/2006 |
| EP | 1 284 777 | 4/2006 |
| EP | 1 171 065 | 3/2007 |
| EP | 1 476 217 | 3/2008 |
| EP | 1 121 163 | 11/2008 |
| EP | 2098257 A1 | 9/2009 |
| EP | 2 311 509 | 4/2011 |
| FR | 1163907 | 10/1958 |
| GB | 114754 | 4/1918 |
| GB | 236350 | 7/1925 |
| GB | 641061 | 8/1950 |
| GB | 1224009 A | 3/1971 |
| GB | 1273342 A | 5/1972 |
| GB | 1400124 | 7/1975 |
| GB | 1549756 A | 8/1979 |
| GB | 2041756 A | 9/1980 |
| GB | 2099306 A | 12/1982 |
| GB | 2195255 A | 4/1988 |
| GB | 2235877 A | 9/1989 |
| GB | 2272645 A | 5/1994 |
| GB | 2273133 A | 6/1994 |
| GB | 2306580 A | 5/1997 |
| GB | 2307180 B | 5/1997 |
| GB | 2329127 B | 3/1999 |
| GB | 2336546 B | 10/1999 |
| GB | 2378392 A | 2/2003 |
| GB | 2415908 A | 1/2006 |
| JP | 59-87824 | 6/1984 |
| JP | 2000-220570 | 8/2000 |
| JP | 2003-165843 | 6/2003 |
| RU | 240188 | 3/1969 |
| SU | 1251912 A1 | 4/1983 |
| SU | 1762940 A1 | 1/1989 |
| WO | WO 80/01139 | 6/1980 |
| WO | WO 80/02182 | 10/1980 |
| WO | WO 83/02054 | 6/1983 |
| WO | WO 84/01904 | 5/1984 |
| WO | WO 87/04626 | 8/1987 |
| WO | WO 89/05133 | 6/1989 |
| WO | WO 90/10424 | 9/1990 |
| WO | WO 90/11795 | 10/1990 |
| WO | WO 91/00718 | 1/1991 |
| WO | WO 91/16030 | 10/1991 |
| WO | WO 92/19313 | 11/1992 |
| WO | WO 92/20299 | 11/1992 |
| WO | WO 93/09727 | 5/1993 |
| WO | WO 94/20041 | 9/1994 |
| WO | WO 94/23677 | 10/1994 |
| WO | WO 95/04511 | 2/1995 |
| WO | WO 95/14451 | 6/1995 |
| WO | WO 95/16416 | 6/1995 |
| WO | WO 96/05873 | 2/1996 |
| WO | WO 96/21410 | 7/1996 |
| WO | WO 97/11658 | 4/1997 |
| WO | WO 97/18737 | 5/1997 |
| WO | WO 99/01173 | 1/1999 |
| WO | WO 99/13793 | 3/1999 |
| WO | WO 99/39671 | 8/1999 |
| WO | WO 00/07653 | 2/2000 |
| WO | WO 00/21586 | 4/2000 |

(56) References Cited

FOREIGN PATENT DOCUMENTS

| | | |
|---|---|---|
| WO | WO 00/42957 | 7/2000 |
| WO | WO 00/50143 A | 8/2000 |
| WO | WO 00/59424 | 10/2000 |
| WO | WO 00/61206 | 10/2000 |
| WO | WO 01/10363 | 2/2001 |
| WO | WO 01/19430 A1 | 3/2001 |
| WO | WO 01/34223 | 5/2001 |
| WO | WO 01/37922 | 5/2001 |
| WO | WO 01/85248 | 11/2001 |
| WO | WO 01/89431 | 11/2001 |
| WO | WO 01/93793 | 12/2001 |
| WO | WO 02/17840 | 3/2002 |
| WO | WO 02/26180 | 4/2002 |
| WO | WO 02/38096 | 5/2002 |
| WO | WO 02/076379 | 10/2002 |
| WO | WO 02/083046 A1 | 10/2002 |
| WO | WO 02/092783 | 11/2002 |
| WO | WO 03/005943 | 1/2003 |
| WO | WO 03/009796 | 2/2003 |
| WO | WO 03/018098 | 3/2003 |
| WO | WO 03/030966 | 4/2003 |
| WO | WO 03/045492 | 6/2003 |
| WO | WO 03/057307 | 7/2003 |
| WO | WO 03/085810 | 10/2003 |
| WO | WO 03/086232 | 10/2003 |
| WO | WO 03/092620 | 11/2003 |
| WO | WO 03/094813 | 11/2003 |
| WO | WO 03/101508 | 12/2003 |
| WO | WO 2004/018020 | 3/2004 |
| WO | WO 2004/024300 | 3/2004 |
| WO | WO 2004/037334 | 5/2004 |
| WO | WO 2004/073566 | 9/2004 |
| WO | WO 2004/081421 | 9/2004 |
| WO | WO 2005/009488 | 2/2005 |
| WO | WO 2005/016179 | 2/2005 |
| WO | WO 2005/025666 | 3/2005 |
| WO | WO 2005/046761 | 5/2005 |
| WO | WO 2005/051461 | 6/2005 |
| WO | WO 2005/070480 | 8/2005 |
| WO | WO 2005/082435 | 9/2005 |
| WO | WO 2005/123170 | 12/2005 |
| WO | WO 2006/048240 | 5/2006 |
| WO | WO 2006/056294 | 6/2006 |
| WO | WO 2006/105892 | 10/2006 |
| WO | WO 2007/024230 | 3/2007 |
| WO | WO 2007/030601 | 3/2007 |
| WO | WO 2008/040681 | 4/2008 |
| WO | WO 2009/066105 | 5/2009 |
| WO | WO 2009/066106 | 5/2009 |

OTHER PUBLICATIONS

U.S. Appl. No. 12/719,715, filed Mar. 8, 2010, published as 2005/0261642 A1, including its ongoing prosecution history, including without limitation Office Actions, Amendments, Remarks, and any other potentially relevant documents).

U.S. Appl. No. 12/832,031, filed Jul. 7, 2010, (published as 2010/0274207 A1) and its ongoing prosecution history, including without limitation Office Actions, Amendments, Remarks, and any other potentially relevant documents.

U.S. Appl. No. 12/744,277, filed Sep. 20, 2010, including its ongoing prosecution history, including without limitation Office Actions, Amendments, Remarks, and any other potentially relevant documents.

U.S. Appl. No. 12/744,218, filed May 21, 2010, including its ongoing prosecution history, including without limitation Office Actions, Amendments, Remarks, and any other potentially relevant documents.

U.S. Appl. No. 12/940,788, filed Nov. 5, 2010, and its ongoing prosecution history, including without limitation Office Actions, Amendments, Remarks, and any other potentially relevant documents.

U.S. Appl. No. 12/719,767, filed Mar. 8, 2010, including its ongoing prosecution history, including without limitation Office Actions, Amendments, Remarks, and any other potentially relevant documents.

U.S. Appl. No. 12/941,390, filed Nov. 8, 2010, including its ongoing prosecution history, including without limitation Office Actions, Amendments (including Preliminary Communication filed Nov. 8, 2010), Remarks, and any other potentially relevant documents.

U.S. Appl. No. 12/744,055, filed May 20, 2010, including its ongoing prosecution history, including without limitation Office Actions, Amendments, Remarks, and any other potentially relevant documents.

U.S. Appl. No. 13/092,042, filed Apr. 21, 2011, including its ongoing prosecution history, including without limitation Office Actions, Amendments (including Preliminary Communication filed Nov. 8, 2010), Remarks, and any other potentially relevant documents.

U.S. Appl. No. 13/217,074, filed Aug. 24, 2011 and its ongoing prosecution history, including without limitation Office Actions, Amendments, Remarks, and any other potentially relevant documents.

U.S. Appl. No. 13/302,980, filed Nov. 22, 2011 and its ongoing prosecution history, including without limitation Office Actions, Amendments, Remarks, and any other potentially relevant documents.

U.S. Appl. No. 13/302,175, filed Nov. 22, 2011 and its ongoing prosecution history, including without limitation Office Actions, Amendments, Remarks, and any other potentially relevant documents.

U.S. Appl. No. 60/559,727, filed Apr. 5, 2004, Richard Scott Weston.

U.S. Appl. No. 60/573,655, filed May 21, 2004, Richard Scott Weston.

U.S. Appl. No. 10/599,720, filed Oct. 6, 2006, Blott et al.

U.S. Appl. No. 12/192,000, filed Aug. 14, 2008, Hartwell et al.

U.S. Appl. No. 13/287,897, filed Nov. 2, 2011, including its ongoing prosecution history, including without limitation Office Actions, Amendments, Remarks, and any other potentially relevant documents.

U.S. Appl. No. 13/287,959, filed Nov. 2, 2011, , including its ongoing prosecution history, including without limitation Office Actions, Amendments, Remarks, and any other potentially relevant documents.

Achterberg, V., Ph.D., Hydroactive dressings and serum proteins: an in vitro study, Journal of Wound Care, February, vol. 5, No. 2, 1996 (pp. 79-82).

Argenta, Louis C., et al., "Vacuum-Assisted Closure: A New Method for Wound Control and Treatment; Clinical Experience", Ann Plas Surg 1997;38:563-577 (Dec. 10, 1996).

Aubrey, D.A., et al., Treatment of the Perineal Wound after Proctectomy by Intermittent Irrigation, Arch. Surg., Oct. 1984, 119, 1141-1144.

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

Biblehimer, Helen L., "Dealing With a Wound that Drains 1.5 Liters a Day," RN, Aug. 1986, pp. 21-23, USA.

Bier, A., Hyperemia as a Therapeutic Agent, *Ed. Dr. Gustavus M. Blech, A. Robertson & Co.*, Chicago 1905, pp. 74-85.

Brubacher, "To Heal a Draining Wound", RN Mar. 1982, 7 pages.

Bucalo et al. "Inhibition of Cell Proliferation by Chronic Wound Fluid." Wound Repair and Regeneration, Miami, 1993, pp. 181-186.

Canadian Office Action for Canadian Application No. 2739605 dated Aug. 22, 2011 in 2 pages.

Chariker, M.E., et al, "Effective Management of Incisional and Cutaneous Fistulae with Closed Suction Wound Drainage," Contemporary Surgery. Jun. 1989, pp. 59-63, vol. 34 USA.

Chinese Office Action dated Aug. 29, 2008 for Patent Application No. 200480032101.1.

(56) References Cited

OTHER PUBLICATIONS

Chintamani, et al., "Half versus full vacuum suction drainage after modified radical mastectomy for breast cancer—a prospective randomized clinical trial", Research Article (Jan. 27, 2005), 1-5.
Costunchenok, BM, Effect of Vacuum on Surgical Purulent Wounds, Vestnik Chirurgia, 1986, 6 pages.
Davydov et al. "Pathogenic Mechanisms of the Effect of Vacuum Therapy on the Course of the Wound Process" pp. 43-46 (Dec. 1990).
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y. et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
EPO, Office Action for EP App. No. 04 791 592.1 dated Jun. 12, 2008.
EPO, Second European Office Action for EP App. No. 04 791 592.1 dated Feb. 10, 2011.
Fleischmann, Vacuum sealing: indication, technique, and results, European Journal of Orthopaedic Surgery & Traumatology (1995), pp. 37-40.
Fleischmann, W. Wund Forum Spezial. IHW '94. "Vakuumversiegelung zur Behandlung von Problemwuden" (with English translation: Vacuum Sealing for Treatment of Problematical Wounds).
Garcia-Rinaldi, R., et al., Improving the Efficiency of Wound Drainage Catheters, Amer. Journ. of Surg., Sep. 1975, pp. 130, 372-373.
Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
International Search Report for International Application No. PCT/GB/2004/004549, dated Feb. 21, 2005.
Japanese Office Action dated Aug. 25, 2009 for Patent Application No. 2006-537411.
Japanese Office Action dated Dec. 15, 2009 for Patent Application No. 2006-537411.
Japanese Office Action dated Jun. 22, 2010 for Patent Application No. 2006-537411.
Japanese Office Action dated Jan. 17, 2012 for Patent Application No. 2010-59188.
Jeter, K.F., et al, "Managing Draining Wounds and Fistulae: New and Established Methods", Chronic Wound Care, pp. 240-246.
Johnson, F.E., An Improved Technique for Skin Graft Placement using a Suction Drain, Surgery, Gynecology and Obstetrics, Dec. 1984, 3 pages.
KCI Inc., If It's Not VAC Therapy, It's Not Negative Pressure Wound Therapy, Jan. 2005.
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Landes, R.R. and I. Melnick, An Improved Suction Device for Draining Wounds, Arch. Surg., May 1972, 104, p. 707.
Linden, Willem van der, et al, "Randomized Trial of Drainage After Cholecystectomy: Suction Versus Static Drainage Through a Main Wound Versus a Stab Incision", American Journal of Surgery, Feb. 1981, vol. 141, pp. 289-294.
Mcfarlane, R.M., The Use of Continuous Suction under Skin Flaps, Br. Journ. Plast. Surg., pp. 77-86.
Mclaughlan, J, et al, "Sterile Microenvironment for Postoperative Wound Care", The Lancet, Sep. 2, 1978, pp. 503-504.
Meyer, W. and V. Schmeiden, Bier's Hyperemic Treatment, Published 1908 W. B. Saunders Company, pp. 44-65.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Nakayama, Y, et al, "A New Method for the Dressing of Free Skin Grafts", Plastic and Reconstructive Surgery, Dec. 1990 pp. 1216-1219, UK.
Nursing75, Wound Suction: Better Drainage with Fewer Problems, Nursing, vol. 5, No. 10, Oct. 1975, pp. 52-55.
Office Action (Final) for U.S. Appl. No. 10/575,875, published as 2007/129,707, dated Jun. 17, 2009 in 19 pages.
Ramirez, O.M., et al., Optimal Wound Healing under Op-Site Dressing, Ideas and Innovations, 73(3), pp. 474-475.
Ranson, J. H. C., et al, "Safer Intraperitoneal Sump Drainage", Surgery, Gynecology & Obstetrics, Nov. 1973, vol. 137, pp. 841-842.
Sames, C.P., Sealing of Wounds with Vacuum Drainage, Br. Med. Journ., Nov. 5, 1977, p. 1223, Correspondence.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).
Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers," The Lancet, Sep. 1983, 532-34.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Swift, et al, "Quorum Sensing in *Aeromonas hydrophila* and *Aeromonas salmoncida*: Identification of LuxRI Homologs AhyRI and AsaRI and Their Cognate N-Acylhomoserine Lactone Signal Molecules," J. Bacteriol., 179(17):5271-5281 (1997).
Teder and Svedman et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005),185-194.
Vijanto, J. and J. Raekallio, Local Hyperalimentation of Open Wounds, Br. J. surg., 1976, 63, 427-430.
Wackenfors, A., et al., Effects of Vacuum-Assisted Closure Therapy on Inguinal Wound Edge Microvascular Blood Flow, *Wound Rep. Reg*, Dec. 2004, 600-606.

(56) References Cited

OTHER PUBLICATIONS

Webb, New Techniques in Wound Management: Vacuum-Assisted Wound Closure, Journal of the American Academy of Orthopaedic Surgeons, v. 10, No. 5, pp. 303-311, Sep. 2002.
Webster's Revised Unabridged Dictionary, published 1913 by C. & G. Merriam Co., definition of Flapper Valve, downloaded from Free Online Dictionary.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
Wu, W.S. et al. Vacuum therapy as an intermediate phase in would closure: a clinical experience, Eur J Plast Surg (2000) 23: pp. 174-177.
US 6,216,701, 04/2001, Heaton et al. (withdrawn).
US 7,186,244, 03/2007, Hunt et al. (withdrawn).
U.S. Appl. No. 13/859,670, filed Apr. 9, 2013, Weston.
U.S. Appl. No. 13/092,446, filed May 24, 2013, Weston.
Alexander, J. Wesley, "Prevention of Wound Infections," The American Journal of Surgery, Jul. 1976, pp. 59-63, vol. 132, USA.
Alper, J.C., et al., An Effective Dressing for a Large, Draining Abdominal wound, *RN*, Dec. 1988, 24-25.
Alper, J.C., et al., Moist Wound Healing under a Vapor Permeable Membrane, *Journ. of Amer. Acad. of Derm.*, Mar. 1983, 8(3), 347-353.
Alper, Joseph, C., "Recent Advances in Moist Wound Healing," Southern Medical Journal, Nov. 1986, pp. 1398-1404, vol. 79, No. 11 USA.
Arnljots et al., "Irrigation Treatment in Split-Thickness Skin Grafting of Intractable Leg Ulcers," Scandinavian Journal of Plastic and Reconstructive Surgery, 1985, vol. 19, pp. 211-213.
Barker, D.E., et al., Vacuum Pack Technique of Temporary Abdominal Closure: A 7-Year Experience with 112 Patients, *Journ. of Trauma: Injury and Critical Care*, Feb. 2000, 4892), 201-207.
Benjamin, P.J., Faeculent Peritonitis: A Complication of Vacuum Drainage, *Br. J. Surg.*, 1980, 67, 453-454.
Berman and Fabiano, Closed Suction Drainage, *Orthopedics*, Mar. 1990, 13(3), 310-314.
Berman, A. T., et al., Comparison Between Intermittent (Spring-Loaded) and Continuous Closed Suction Drainage of Orthopedic Wounds: A Controlled Clinical Trial, *Orthopedics*, Mar. 1990, 13(3), 9 pgs.
Besst, J.A., Wound Healing—Intraoperative Factors, *Nursing Clinics of North America*, Dec. 1979, 14(4), 701-712.
Bischoff, et al., Vacuum-Sealing Fixation of Mesh Grafts, *Euro. Journ. Plast. Surg.*, Jul. 2003, 26(4), 189-190, Abs. Downloaded from internet Apr. 6, 2006.
Britton, B.J., et al., A Comparison Between Disposable and Non-Disposable Suction Drainage Units: A Report of a Controlled Trial, *Br. J. Surg.* 1979, 66, 279-280.
Brummelkamp, W.H., et al, "High-vacuum drainage and primary perineal wound closure in abdominoperineal excision of the rectum", The Netherlands Journal of Surgery, 1991 pp. 236-238, Netherlands.
Burdette-Taylor, S.R., Use of the Versatile One (V1) for Closed Suction Drainage to Stimulate Closure in Chronic Wounds in Home Care, Case Study Presentation, 2003, 2 pgs.
Carroll, P.L., The Principles of Vacuum and its Use in the Hospital Environment, 2nd Ed., 1986, 30p.
Chardack, et al., Experimental studies on Synthetic Substitutes for Skin and Their Use in the Treatment of Burns, vol. 155, No. 1 pp. 128-136.
Chua Patel, C.T., et al., Vacuum-Assisted Closure, *AJN*, Dec. 2000, 100(12), 45-49.
Cooper, S.M. and E. Young, Topical Negative Pressure, *Commentary, International Journal of Dermatology 2000*, 39, 892-898.
Crisp, W.J. and A. Gunn, Granuflex Dressings for Closed Surgical Wounds Combined with Suction Drainage, *Annals of the Royal College of Surgeons of England*, 1990, 72, p. 76.
Cucuroos, Y.C., Vacuum Drainage of Post Operative Wounds, *Kiev Army Hospital, Dept. of Hospital Surgery, Kiev medical University*, 64-65 (in Russian with English translation).
Curtin, L.L., Wound Management: care and Cost—an Overview, *Nursing Management*, Feb. 1984, 15(_), 22-25.
Davidov, Y.A., et al. Justifying the Usage of Force Early Secondary Sutures in treatment of Purulent Wounds by the Vacuum Therapy, *Vestnik Chirurgia 1990, March Edition*, 126-129 (*in Russian with English translation*).
De Lange, M.Y., et al., "Vacuum-Assisted Closure: Indications and Clinical Experience", Eur J Plast Surg (2000) 2;178-182 (Feb. 9, 2000).
Domkowski, P.W., et al., Evaluation of Vacuum-Assisted Closure in the Treatment of Poststernotomy Mediastinitis, *Journ. of Thorac. and Cardiovascular Surg.*, Aug. 2003, 126(2), 386-390.
Doss, Mirko, et al., Vacuum-Assisted Suction Drainage Versus Conventional Treatment in the Management of Poststernotomy Osteomyelitis, *Euro. Journ. Cardio-Thoracic. Surg.* 22((2002) 934-938.
Eaglstein, W.H., et al., Wound Dressings: Current and Future, *Clin. and Exper. Approaches to Dermal and Epidermal Repair: Normal and Chronic Wounds*, 1991, 257-265.
ECRI, Target Report, Negative Pressure Wound Therapy for Chronic Wounds, Jan. 24, 2006, 1-7, Downloaded from internet, http://www.target.ecri.org/summary/detail.aspx?dox_id=1155.
Elwood, E.T., and D.G. Bolitho, Negative-Pressure Dressings in the Treatment of Hidradenitis Suppurative, *Annals of Plastic Surgery*, Jan. 2001, 46(1), 49-51.
Fabian, T.S., The Evaluation of Subatmospheric Pressure and Hyperbaric Oxygen in Ischemic Full-Thickness Wound Healing, *Ischemic Full-Thickness Wound Healing*, Dec. 2000, 66(12), 1136-1143.
Fay, M.F., Drainage Systems: Their Role in Wound Healing, *AORN Journal*, Sep. 1987, 46(3), 442-455.
Fingerhut, A., et al., Passive vs. Closed Suction drainage after Perineal Wound Closure Following Abdominoperineal Rectal Excision for Carcinoma, *Dis Colon Rectum*, Sep. 1995, 926-932.
Firlit, C.F. and J.R. Canning, Surgical Wound Drainage: A Simple Device for Collection, *Journ. of Urology*, Aug. 1972, 108, p. 327.
Fleischmann, W. Acta Orthopaedical Belgica, "Treatment of Bone and Soft Tissue Defects in Infected Nonunion," vol. 58, Suppl. I-1992, pp. 227-235.
Fleischmann, W. Unfall Chirurg, Springer-Variag, "Vakuumversiegelung zur Behandlung des Weichteilschadens bei offenen Frakturen," (English abstract, no English translation), 1993, pp. 488-492.
Fox, J.W. and G.T. Golden, The Use of Drains in Subcutaneous Surgical Procedures, *Amer. Journ. of Surg*, Nov. 1976, 132, 673-674.
Gorica Zivadinovic, et al., Vacuum Therapy in the Treatment of Peripheral Blood Vessels, Conference Papers of the 5$^{th}$ Timok Medical Days, Majdanpek, 1986 pp. 161-164.
Grobmyer, et al., High-Pressure Gradients Generated by Closed-Suction Surgical Drainage Systems, *Surg. Infect. (Larchmt)*, Autumn 2002, 3(3), 245-249, Abs., Downloaded Nov. 30, 2003.
Gwan-Nulla, D.N. and R.S. Casal, Toxic Shock Syndrome Associated with the Use of the Vacuum-Assisted Closure Device, *Ann. Plast. Surg.*, Nov. 2001, 47(5), 552-554.
Johnson, F.E., An Improved Technique for Skin Graft Placement using a Suction Drain, *Surgery, Gynecology & Obstetrics*, Dec. 1984, 159(6), 584-585.
Kazan Medical Institute Doctors, A Gadget to Bring the Wound Edges Close, 78-79 (in Russian with English translation). Aug. 20, 1985.
KCI, Inc., The V.A.C. System, 2000-2001, Brochure, 2 pgs.
Kim, S.H., et al., Wangensteen Suction Drainage, apparatus in Neurosurgical Practice, *Dept. of Neurosurgery, Yonsei University of College of Medicine*, Seoul, Korea, 1975, 159-160, Abs. (in Korean and Abstract in English).
Kloth, L.C. and J.M. McCulloch, Wound Healing Alternatives in Management, 3rd Ed., Chap. 10, 339-352, 2002.
Knight, Marie Ray, A Second Skin for Patients with Large Draining Wounds, Nursing, Jan. 1976, p. 37, USA.

(56) References Cited

OTHER PUBLICATIONS

Kremlin Papers, A Collection of Published Studies Complementing the Research and Innovation of Wound Care, from *Vestnik Khirurgii*, BlueSky Publishing, A Div. of BlueSky Medical Group Inc., 2004. 17 pages.
Landis, E.M. and J.H. Gibbon, Jr., The Effects of Alternate Suction and Pressure on Blood Flow to the Lower Extremities, Alternate Suction and Pressure, J Clin Invest. Sep. 1933, 12(5): 925-961.
Lumley, J.S.P., et al., The Physical and bacteriological Properties of Disposable and Non-Disposable Disposable Suction Drainage Units in the Laboratory, Br. J. Surg., 1974, 61, 832-837.
Lundvall, J. and T. Lanne, Transmission of Externally applied Negative pressure to the Underlying Tissue: A Study on the Upper Arm of Man, *Acta Physiol. Scand.* 1989, 136, 403-409.
Maitland and Mathieson, Suction Drainage, *Brit. J. Surg,*, Mar. 1970, 57(3), 195-197.
Mendez-Eastman, S., Guidelines for Using Negative Pressure Wound Therapy, *Advances in Skin & Wound Care*, 14(6), Nov./Dec. 2001, 314-325.
Meyer, W. & Schmieden, V., "In Surgery, Medicine, and the Specialties a Manual of its Practical Application", *Bier's Hyperemic Treatment*, Second Revised Edition, W B. Saunders Company 1909.
Milsom, I. and A. Gustafsson, An Evaluation of a Post-Operative Vacuum Drainage System, *Curr. Med. Res. Opin.* (1979), 6, 160-164.
Moloney, G. E., "Apposition and Drainage of Large Skin Flaps by Suction", ANZ Journal of Surgery vol. 26, Issue 3, Feb. 1957, pp. 173-179.
Morykwas, M.J., et al., Effects of Varying Levels of Subatmospheric Pressure on the Rate of Granulation Tissue Formation in Experimental Wounds in Swine, *Abs., Ann. Plast. Surg.* 2001, 47: 547.
Moserova, J. and E. Houskova, The Healing and Treatment of Skin Defects, 1989, 116-143.
Mulder, G.D., Ed., et al., Clinicians' Pocket Guide to Chronic Wound Repair, *Wound Healing Publications*, Spartanburg, SC, 1991, 54-55.
Mullner, T., et al., The Use of Negative Pressue to Promote the Healing of Tissue Defects: A Clinical Trial Using the Vacuum Sealing Technique, *Br. J. Plast. Surg.*, Apr. 1997, 51(1), 79, Abs.
Nakayama et al., Ann. Plast. Surg., 26: 499-502 (1991), "A New Dressing Method for Free Skin Grafting in Hands."
Nakayama, Yoshio, et al., A New Method for Dressing of Free Skin Grafts, New Method for Free Skin Grafting, vol. 86, No. 6 Jun. 12, 1990.
Nasser, A.N., The Use of the Mini-Flap Wound Suction Drain in maxillofacial surgery, *Annals of the Royal College of Surgeons of England*, 1986, 68, 151-153.
Navsaria, P.H., et al., Temporary Closure of Open Abdominal Wounds by the Modified Sandwich-Vacuum Pack Technique, *Br. Journ. Surg.*, 2003, 90, 718-722.
Nicholas, J.M., Options for Management of the Open Abdomen, Presentation from Emory University School of Medicine, 66 pgs. Invited Speaker American College of Surgeons 32nd Annual Spring Meeting, General Session 12—Presentation and Panel Discussion on the Open Abdomen in General Surgery—How Do You Close the Abdomen When You Can't—Bostom Marriott Copley Place Hotel, Boston, MA Apr. 26, 2004.
Ohotskii, V.P., et al., Usage of Vacuum Suction During the Primary Surgical Debridement of Open Limb Injuries, *Sovetskaya Medicina*, Jan. 1973, 17-20 (in Russian with English translation).
Putney F. Johnson, "The Use of Continuous Negative Pressure after Laryngectomy and Radical Neck Dissection", Surgery, Gynecology & Obstetrics, Aug. 1956, pp. 244-246, USA.

Raffl, Arthur B., "Use of Negative Pressure Under Skin Flaps After Radical Mastectomy," Dept. of Surgery, State Univ. of N.Y., College of Medicine, Syracuse, NY, Submitted for publication Apr. 1953, p. 1048, USA.
Reimann, D., et al., Successful Treatment Due to Vacuum Seal Technique of a Severe Scedosporium Apiospermum Skin Infection in a Renal Transplant Recipient, *Nephroi. Dial. Transplant*, 2004, 19 (1), 245-248.
Robertson, "The Influence upon Wound Contraction of a Negative Interstitial Fluid Pressure Within Granulation Tissue," Journal of Anatomy, 1969, vol. 105, No. 1, pp. 189.
Schaffer, D.B., Closed Suction Wound Drainage, Nursing97, Nov., Downloaded from Internet www.springnet.com, 62-64. 1997.
Shaer, W.D., et al., Inexpensive Vacuum-Assisted Closure Employing a Conventional Disposable Closed-Suction Drainage System, *Plastic and Reconstructive Surgery*, Jan. 2001, 292.
Smith, L.A., et al., Vacuum Pack Technique of Temporary Abdominal Closure: A Four-Year Experience, *Amer. Surg.*, Dec. 1997, 63(12), 1102-1108.
Spengler, Michael D., el al, "Performance of Filtered Sump Wound Drainage Tubes", Surgery, Gynecology & Obstetrics, Mar. 1982, pp. 333-336, vol. 54, USA.
Tennant, C.E., "The Use of Hyperemia in the Postoperative Treatment of Lesions of the Extremities and Thorax," Jour. A. M. A., May 8, 1915, pp. 1548-1549.
Tenta, L.T., et al., Suction Drainage of Wounds of the Head and Neck, *Surg. Gyn. & Ob.*, Dec. 1989, 169, p. 558.
Urschel, J.D., et al., The Effect of Mechanical Stress on Soft and Hard Tissue Repair; A Review, *Br. Journ. Plast. Surg.*, 1988, 41, 182-186.
Usypov, Y. N. and M.V. Ephfanov, Active Drainage of wounds, Dept. of Hospital Surgery, Army Medical Academy, Leningrad, *Vestnik Chirurgia 1987*, April Edition, 42-45 (in Russian with English translation).
Valenta, A.L., Using the Vacuum Dressing Alternative for Difficult Wounds, *AIN*, Apr. 1994, 44-45.
Van Heurn, L.W.E. and P.R.G. Brink, Prospective Randomized Trial of High versus Low Vacuum Drainage after Axillary Lymphadenectomy, *Br. Journ. Surg.* 1995, 82, 931-932.
Williams, et al., Survey of the Use of Suction Drains in head and Neck Surgery and Analysis of Their Biomechanical Properties, *J. Otolaryngol.*, Feb. 2003, 32(1), 16-22, Abs. Downloaded from internet Nov. 30, 2003.
Windows on Medical Technology, Vacuum-Assisted Wound Closure for Chronic and Acute Wounds,, *ECRI Health Technology Assessment Information Service*, Oct. 2000, 38, 1-21.
Wolthuis, Roger A., et al, "Physiological Effects of Locally Applied Reduced Pressure in Man," Physiological Reviews, Jul. 1974, pp. 566-595 vol. 54, No. 3, USA.
Worth, M.H. and H.W. Andersen, The Effectiveness of Bacterial Filtration in Vented Wound Drains, *Journ. of Surg. Research*, 1979, 27, 405-407.
Wu, P., et al., In Vitro Assessment of Water Vapour Transmission of Synthetic Wound Dressings, *Biomaterials*, 1995, 16(3), 171-175.
Yu A. Davydov, et al., Vacuum Therapy in treatment of Acute Purulent Diseases of Soft Tissues and Purulent Wounds, Vestnik Khirurgii, (Surgeon's Herald), Medicine Publishers, 1986.
International Preliminary Report for International Application No. PCT/GB/2004/004549, Dated Dec. 20, 2005.
International Search Report for International Application No. PCT/GB/2004/004549, Dated Feb. 21, 2005 in 4 pages.
Kendall ULTEC Hydrocolloid Dressing (4"×4"), product ordering page, web page downloaded Jul. 13, 2014.
Protz, Kerstin: "Modern Wundauflagen unterstutzen Heilungsprozess", Wundversorgung: Indikation und Anwendung, Geriatrie Journal Apr. 2005, pp. 3333-3339.

* cited by examiner

WOUND CLEANSING APPARATUS IN-SITU

CROSS-REFERENCE TO RELATED APPLICATIONS

This application is a continuation of U.S. patent application Ser. No. 12/940,788, published as US 2011/0054423 A1 and filed on Nov. 5, 2010, which is a continuation of U.S. patent application Ser. No. 10/575,871, filed on Jan. 29, 2007 and now issued as U.S. Pat. No. 7,964,766, which is a U.S. National Phase of the PCT International Application No. PCT/GB04/04549, filed on Oct. 28, 2004, and which claims priority to application GB 0325129.5, filed on Oct. 28, 2003. The entirety of these preceding disclosures are hereby incorporated by reference.

FIELD OF THE INVENTION

The present invention relates to apparatus and a medical wound dressing for cleansing wounds, and a method of treating wounds using such apparatus.

It relates in particular to such an apparatus, wound dressing and method that can be easily applied to a wide variety of, but in particular chronic, wounds, to cleanse them of materials that are deleterious to wound healing, whilst retaining materials that are beneficial in particular to wound healing.

BACKGROUND OF THE INVENTION

Before the present invention, aspirating and/or irrigating apparatus were known, and tended to be used to remove wound exudate during wound therapy. In known forms of such wound therapy, the offtake from the wound, especially when in a highly exuding state, is voided to waste, e.g. to a collection bag.

Materials deleterious to wound healing are removed in this way. However, materials that are beneficial in promoting wound healing, such as growth factors, cell matrix components, and other physiologically active components of the exudate from a wound are lost to the site where they can be potentially of most benefit, i.e. the wound bed, when such therapy is applied.

Such known forms of wound dressing and aspiration and/or irrigation therapy systems thus often create a wound environment under the dressing that may result in the loss of optimum performance of the body's own tissue healing processes and in slow healing, and/or in weak new tissue growth that does not have a strong three-dimensional structure adhering well to and growing from the wound bed. This is a significant disadvantage, in particular in chronic wounds.

It thus would be desirable to provide a system of therapy which
a) can remove materials deleterious to wound healing from wound exudate, whilst
a) retaining materials that are beneficial in promoting wound healing in contact with the wound bed.

Dialysis is a known method of treating bodily fluids such as blood ex vivo, to cleanse them of materials that are deleterious to the body systemically. Removal of such materials by contact with the dialysate is the prime purpose of dialysis, whilst also retaining materials such as blood, cells and proteins. Other materials that may have an additional positive therapeutic action are potentially lost to the system through the dialysis membrane, which is also permeable to them. The balance of such materials in the bodily fluid in recirculation may thus be further depleted.

SUMMARY OF THE INVENTION

It would be desirable to provide a system of therapy that can remove materials deleterious to wound healing from wound exudate, without substantially diluting materials that are beneficial in promoting wound healing in contact with the wound bed, and which can continuously supply and recirculate such materials to the wound simultaneously.

Dialysis for treating bodily fluids is also a systemic therapy, since the treated fluid is returned to within the body. This is in contrast to a topical therapy in which the treated fluid is recycled outside the body, e.g. to a wound.

Dialysis also requires large amounts either of bodily fluids, such as blood, or dialysate, and consequently the relevant devices tend not to be portable. Even when in a highly exuding state, chronic wounds produce relatively little fluid to be treated compared with internal bodily systems and relatively little materials that are beneficial in some therapeutic aspect to be retained in the wound and/or its environment.

It is an object of the present invention
a) to obviate at least some of the abovementioned disadvantages of known aspiration and/or irrigation therapy systems, and
b) to provide a system of therapy which can
  i) remove materials deleterious to wound healing from wound exudate, whilst
  ii) retaining materials that are beneficial in promoting wound healing in contact with the wound bed.
It is a further object of the present invention
a) to obviate at least some of the abovementioned disadvantages of known dialysis systems, and
b) to provide a system of therapy which can remove materials deleterious to wound healing from wound exudate, whilst retaining materials that are beneficial in promoting wound healing in contact with the wound bed,
c) without affecting the body systemically.
It is a yet further object of the present invention
a) to obviate at least some of the abovementioned disadvantages of known dialysis systems, and
b) to provide a system of therapy which can remove materials deleterious to wound healing from wound exudate, whilst retaining materials that are beneficial in promoting wound healing in contact with the wound bed, and
c) is portable.

Vascular supply to, and circulation in, tissue underlying and surrounding the wound is often compromised. It is a further object of the present invention to provide a system of therapy that retains and supplies therapeutically active amounts of materials that are beneficial in reversing this effect whilst removing deleterious materials, thereby promoting wound healing.

Thus, according to a first aspect of the present invention there is provided an apparatus for cleansing wounds, comprising
a conformable wound dressing, having
a backing layer which is capable of forming a relatively fluid-tight seal or closure over a wound and
characterised in that it also comprises
a) a cleansing means for selectively removing materials that are deleterious to wound healing from wound exudate, which means is under the backing layer and sits in the underlying wound in use and b) a moving device for moving fluid through the cleansing means, and c) optionally bleed means for bleeding the cleansing means.

The term 'bleed means for bleeding the cleansing means' includes any bleed means that is in fluidic communication with the cleansing means.

Materials deleterious to wound healing are removed by the cleansing means, and the cleansed fluid remains in and/or is returned to the wound.

The fluid thus retains naturally occurring materials in the wound exudate that are potentially beneficial to wound healing in therapeutically active amounts The apparatus for cleansing wounds of this first aspect of the present invention is based on this principle: by moving fluid through the cleansing means, the moving device continually brings materials that are deleterious to wound healing and the cleansing means into mutual dynamic contact, rather than relying on the passive movement of such materials, e.g. by diffusion under a chemical potential gradient in a fluid. Their removal from the wound exudate occurs more rapidly with such fluid movement.

There are various embodiments of the apparatus of the first aspect of the present invention for different types of application, including in particular those that are described in detail hereinafter. No matter how different they may be, it is believed that they may be classified into the following functional types, typified by which fluid passes through the cleansing means:

1. A 'single-phase system'
   In this, the fluid that is moved through the means for fluid cleansing is wound exudate optionally mixed with an irrigant. This passes into, through and out of the cleansing means, e.g. a chamber under the backing layer, and back to the wound bed. Materials deleterious to wound healing pass into and are removed by the means for fluid cleansing before return of the cleansed fluid to the wound bed.

2. A 'multiple-phase system'
   In this, the wound exudate remains in the wound, and does not pass into the cleansing means on a macro-scale. The means for fluid cleansing often comprises a chamber containing a second, cleansing fluid, most usually a fluid (dialysate) phase. The latter is separated from the wound exudate by means of a permeable integer, for example often a polymer film, sheet or membrane. The fluid that is moved through the means for fluid cleansing by the device for moving fluid is the cleansing fluid and/or the wound exudate optionally mixed with irrigant.

In both single- and multiple-phase systems, it may be appropriate to design and run the device to move fluid through the wound or the cleansing means to operate the system as a 'circulating system'.

In this, the relevant fluid passes through the cleansing means one or more times in only one direction.

Alternatively, where appropriate it may be provided in the form of a 'reversing system'. That is, the relevant fluid passes through the cleansing means at least once in opposing directions.

The apparatus of the first aspect of the present invention may however in different types of application be operated both as a circulating system and as a reversing system, in which the relevant fluid passes through the cleansing means at least once in the same and in opposing directions. (See FIG. 2 hereinafter).

The type of cleansing means may determine the appropriate design and mode of running the present apparatus.

The cleansing means may as desired be operated as a 'single-pass system', i.e. the relevant fluid passes through the cleansing means only once.

Alternatively, where appropriate it may be provided in the form of a 'multiple-pass system', in which the relevant fluid passes through the cleansing means and/or over the wound bed several times.

It will be seen that the combination of these parameters create a number of main embodiments of the present invention. In summary, these are:

1. A 'single-phase system'
   a) as a 'circulating system', in which the wound exudate and optionally irrigant passes through the cleansing means one or more times in only one direction (Examples of such a system are shown in FIGS. 2, 4, 8, 9, 11 and 15 hereinafter.), or
   b) as a 'reversing system', i.e. the wound exudate and optionally irrigant passes through the cleansing means at least once in opposing directions. (Examples of such a system are shown in FIGS. 1, 2, 3, 6, 7, 10 and 14 hereinafter.)
   This type of cleansing may be operated as a
   i) 'single-pass system', i.e. the relevant fluid passes through the cleansing means only once, or
   ii) as 'multiple-pass system', in which the relevant fluid passes through the cleansing means and/or over the wound bed several times.

2. A 'multiple-phase system'
   a) as a 'circulating system', in which
      (i) the wound exudate and optionally irrigant and/or
      (ii) a cleansing fluid
      each passes through the cleansing means one or more times in only one direction (Examples of such a system are shown in FIGS. 12 and 13 hereinafter.), or
   b) as a 'reversing system', i.e.
      (i) the wound exudate and optionally irrigant and/or
      (ii) a cleansing fluid
      each passes through the cleansing means at least once in opposing directions.
   This type of cleansing may be operated as a
   i) 'single-pass system', i.e. the relevant fluid passes through the cleansing means only once, or
   ii) as 'multiple-pass system', in which the relevant fluid passes through the cleansing means and/or over the wound bed several times.

In such a 'multiple-phase system', where both the cleansing fluid and/or the wound exudate optionally mixed with irrigant are moving, the flows may be cocurrent or countercurrent, preferably countercurrent.

Examples of such circulating systems are shown in:
FIGS. 12a and 13 in which the exudate is static and a cleansing fluid passes through the cleansing means one or more times in only one direction, and
FIG. 12b, in which the exudate and optionally irrigant and a cleansing fluid each pass through the cleansing means one or more times in only one direction, here countercurrent to each other.

The general features of the dressing of the present invention will now be described, followed by specific features related to specific cleansing means within the dressing.

In all embodiments of the apparatus of this first aspect of the present invention for cleansing wounds, a particular advantage is the tendency of the wound dressing to conform to the shape of the bodily part to which it is applied.

The wound dressing comprises a backing layer with a wound-facing face which is capable of forming a relatively fluid-tight seal or closure over a wound.

The term 'relatively fluid-tight seal or closure' is used herein to indicate one which is fluid- and microbe-impermeable and permits a positive or negative pressure of up to 50% atm., more usually up to 15% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the necessary fluids.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof;

polysiloxanes;

polyesters, such as polycarbonates;

polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound. It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound.

This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage. (A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable).

This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the wound is removed prior to application of radiation of an appropriate wavelength to the flange or lip.

If the periphery of the wound dressing, outside the relatively fluid-tight seal, that bears an adhesive film to attach it to the skin around the wound, is of a material that has a high moisture vapour permeability or is a switchable material, then the adhesive film, if continuous, should also have a high or switchable moisture vapour permeability, e.g. be an adhesive such as used in Smith & Nephew's Allevyn™, IV3000™ and OpSite™ dressings.

In a number of main embodiments of the present invention (summarised above), irrigant and/or wound exudate is moved in and out of the dressing.

This may be done under negative pressure on the dressing. Such a vacuum may be used to hold the wound dressing in place in a fluid-tight seal around the periphery of the wound-facing face of the wound dressing.

This removes the need for adhesives and associated trauma to the patient's skin, and the wound dressing may be merely provided with a silicone flange or lip to seal the dressing around the wound.

Alternatively, the flow of irrigant and/or wound exudate in and out of the dressing may be under positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose.

Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheaths, wraps, stockings and hose.

The latter include, e.g. elastic tubular hose or elastic tubular stockings that are a compressive fit over a limb wound to apply suitable pressure to it when the therapy is applied in this way.

Suitable examples also include inflatable cuffs, sleeves, jackets, trousers, sheaths, wraps, stockings and hose that are a compressive fit over a limb wound to apply suitable pressure to it when the therapy is applied in this way.

Such means may each be laid out over the wound dressing to extend beyond the periphery of the backing layer of the wound dressing.

As appropriate they may be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound, Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit.

It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound.

The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

As noted above, the cleansing means for selectively removing materials that are deleterious to wound healing from wound exudate, which means is under the backing layer and sits in the underlying wound in use, often comprises a chamber. A permeable integer, e.g. a sheet, film or membrane, forms part of the chamber wall.

In single-phase systems, the device to move fluid moves wound exudate in and out of the cleansing means through the permeable integer, either as a 'circulating system' or a reversing system.

In two-phase systems, the chamber contains a cleansing fluid, most usually a fluid (dialysate) phase. The latter is separated from the wound exudate by means of the permeable integer. The fluid that is moved within the means for fluid cleansing by at least one device for moving fluid is the cleansing fluid. and/or the wound exudate optionally mixed with irrigant.

The general features of the cleansing means of the present invention will now be described, followed by specific features related to specific cleansing means within the dressing.

The cleansing chamber is a resiliently flexible, e.g. elastomeric, and preferably soft, structure with good conformability to wound shape.

It is favourably urged by its own resilience against the backing layer to apply gentle pressure on the wound bed.

The cleansing chamber may be integral with the other components of the dressing, in particular the backing layer.

Alternatively, it may be permanently attached to them/it, with an adhesive film, for example, or by heat-sealing, e.g. to a flange or lip extending from the proximal face, so as not to disrupt the relatively fluid-tight seal or closure over the wound that is needed.

Less usually, the cleansing chamber is releasably attached to the backing layer, with an adhesive film, for example, or these components may be a push, snap or twist-lock fit with each other.

The cleansing chamber and the backing layer may be separate structures, permanently unattached to each other.

It may be in the form of, or comprise one or more conformable hollow bodies defined by a film, sheet or membrane, such as a bag, cartridge, pouch or other like structure.

The film, sheet or membrane, often has a (generally uniform) thickness of up to 1 mm, preferably up to 500 micron, more preferably from 20 micron to 500 micron minimum thickness, and is often resiliently flexible, e.g. elastomeric, and preferably soft.

Such a film, sheet or membrane is often integral with the other components of the dressing, in particular the backing layer, or permanently attached to them/it, with an adhesive film, for example, or by heat-sealing, e.g. to a flange.

However, when used herein the term 'chamber' includes any hollow body or bodies defined by a film, sheet or membrane, and is not limited to a bag, pouch or other like structure.

It may be formed of a film, sheet or membrane of a polymeric material is in a more convoluted form.

This may be in the form of elongate structures, such as pipes, tubes hollow fibres or filaments or tubules, e.g. in an array with spaces therebetween, running between an inlet and an outlet manifold.

The chamber, especially when it is a bag, cartridge, pouch or other like structure in which the cleansing fluid is contained, may suitably fill much or all of the wound space when in use during wound therapy. It may be desired to limit the remaining wound space volume under the backing layer with a filler where this is not the case, or to adjust the volume of the chamber to do so.

Where the chamber and the backing layer are separate structures, not directly attached to each other, such a filler may conveniently lie between the chamber and the backing layer to separate the structures, or within the chamber, so that the chamber may lie directly in contact with the wound bed.

The filler is favourably a resiliently flexible, e.g. elastomeric, and preferably soft, structure with good conformability to wound shape. The chamber may be urged by its own resilience and that of the filler to apply gentle pressure on the wound bed.

Examples of suitable forms of such wound fillers include foams formed of a suitable material, e.g. a resilient thermoplastic. Preferred materials for the present wound dressing include reticulated filtration polyurethane foams with small apertures or pores. (Examples of such a filler are shown in FIGS. 7, 10, 11 and 13 hereinafter.)

Alternatively or additionally, it may be in the form of, or comprise one or more conformable hollow bodies defined by a film, sheet or membrane, such as a bag, pouch or other structure, filled with a fluid or solid that urges it to the wound shape.

Examples of suitable fluids contained in the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials. Examples also include aerosol foams, where the gaseous phase of the aerosol system is air or an inert gas, such as nitrogen or argon, more usually air, at a small positive pressure above atmospheric; and solid particulates, such as plastics crumbs.

Such a filler may be inflatable and deflatable with the fluid, such as a gas, e.g. air or nitrogen, or a liquid, such as water or saline, to apply varying pressure to the chamber and wound space if provided with one or more inlet and/or outlet pipes.

Of course, if the backing layer is a sufficiently conformable and/or e.g. a downwardly dished sheet, the backing layer may lie under the wound filler, rather than vice versa. FIG. 6 shows such a resiliently flexible, balloon filler, which is inflatable and deflatable with a fluid, defined by the backing layer and a rigid polymer dome that is impermeable and permanently attached to the distal face of the backing layer In this type of layout, in order for the wound filler to urge the wound dressing towards the wound bed, it will usually have to be firmly adhered or otherwise releasably attached to the skin around the wound. This is especially the case in those embodiments where the wound filler and the backing layer are separate structures, permanently unattached to each other. FIG. 7 shows a variant of the apparatus with such a resiliently flexible balloon filler above the backing layer.

The specific nature of the chamber will depend largely on the type of cleansing means that is employed.

The apparatus of the invention for aspirating, irrigating and/or cleansing wounds is provided with means for fluid cleansing, which may be a) a single-phase system, such as an ultrafiltration unit, or a chemical adsorption unit; or
b) a two-phase system, such as a dialysis unit.

In the former, fluid from the wound passes through a single flow path in which materials deleterious to wound healing are removed and the cleansed fluid, still containing materials that are beneficial in promoting wound healing is returned to the wound.

Examples of such systems are shown in FIGS. 1 and 2 hereinafter.

The means for fluid cleansing in such a system may include a macro- or microfiltration unit, which appropriately comprises one or more macroscopic and/or microscopic filters. These are to retain particulates, e.g. cell debris and micro-organisms, allowing proteins and nutrients to pass through.

The membrane may preferably be of a hydrophilic polymeric material, such as a cellulose acetate—nitrate mixture, polyvinylidene chloride, and, for example hydrophilic polyurethane.

Examples of less preferred materials include hydrophobic materials also including polyesters, such as polycarbonates, PTFE, and polyamides, e.g. 6-6 and 6-10, and hydrophobic polyurethanes, and quartz and glass fibre.

It has microapertures or micropores, the maximum cross-dimension of which will largely depend on the species that are to be selectively removed in this way and those to which it is to be permeable.

The former may be removed with microapertures or micropores, e.g. typically with a maximum cross-dimension in the range of 20 to 700 micron, e.g. 20 to 50 nm (for example for undesired proteins), 50 to 100 nm, 100 to 250 nm, 250 to 500 nm and 500 to 700 nm.

Alternatively, this part of a means for wound exudate cleansing may be essentially a stack of such filters connected in series with decreasing cross-dimension of the apertures or pores in the direction of the fluid flow.

It may include an ultrafiltration unit, which appropriately comprises one or more ultrafiltration filters, such as one in which the cleansing integer is a filter for materials deleterious to wound healing, for example a high throughput, low protein-binding polymer film, sheet or membrane which is selectively impermeable to materials deleterious to wound healing, which are removed and the cleansed fluid, still containing materials that are beneficial in promoting wound healing is passed by it.

The permeable integer in such a system may be a selective low pass' system film, sheet or membrane with relatively small apertures or pores.

Suitable materials for the filter include those organic polymers listed above for macro- and micro-filters.

It will be appropriate to design and run the apparatus with this type of cleansing means as a 'circulating system', in which the relevant fluid passes through the cleansing means one or more times in only one direction, since this is necessary for retaining the filter residue out of the wound exudate.

(It would be inappropriate to run the system in the form of a 'reversing system', since the fluid passing through the cleansing means at least once in the reverse direction would return these materials into the wound.)

The filter integer may be a flat sheet or membrane of a polymeric material, or (less usually) in a more convoluted form, e.g. in the form of elongate structure, such as pipes, tubules, etc.

It may be intended that respectively the chamber or the dressing is disposable. In such case, the device for moving fluid through the means for wound exudate cleansing is then started and run until no significant amounts of materials deleterious to wound healing remain in the wound.

The dressing and/or the cleansing chamber under the backing layer is then removed and discarded, to remove the materials deleterious to wound healing from wound exudate.

A single-phase system cleansing means may comprise a chemical adsorption unit, for example one in which a particulate, such as a zeolite, or a layer, e.g. of a functionalised polymer has sites on its surface that are capable of removing materials deleterious to wound healing on passing the fluid from the wound over them.

The materials may be removed, e.g. by destroying or binding the materials that are deleterious to wound healing, by, for example chelators and/or ion exchangers, and degraders, which may be enzymes.

In this type, the chamber wall film, sheet or membrane is not an integer selectively permeable to materials deleterious to wound healing. The chamber, however, contains one or more materials that can remove materials deleterious to wound healing from wound exudate, by being antagonists to such species.

For example, where the wound exudate contains
proteases, such as serine proteases, e.g. elastase, and thrombin; cysteine proteases, matrix metalloproteases, e.g. collagenase; and carboxyl (acid) proteases;
endotoxins, such as lipopolysaccharides;
inhibitors of angiogenesis such as thrombospondin-1 (TSP-1), plasminogen activator inhibitor, or angiostatin (plasminogen fragment);
pro-inflammatory cytokines such as tumour necrosis factor alpha (TNFα) and interleukin 1 beta (IL-1β),
oxidants, such as free radicals, e.g., e.g. peroxide and superoxide; and metal ions, e.g. iron II and iron III; all involved in oxidative stress on the wound bed, or
basic or acidic species which adversely affect the pH in the wound exudate, such as protons,
the cleansing chamber may contain, behind the permeable integer at least one of the following antagonists as appropriate that is captive in a part of the chamber where it can be in contact with the irrigant and/or wound exudate:
protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide; cysteine protease inhibitors; matrix metalloprotease inhibitors; and carboxyl (acid) protease inhibitors;
binders and/or degraders, such as anti-inflammatory materials to bind or destroy lipopolysaccharides, e.g. peptidomimetics;
anti-oxidants, such as 3-hydroxytyramine (dopamine), ascorbic acid (vitamin C), vitamin E and glutathione, and stable derivatives thereof, and mixtures thereof; to relieve oxidative stress on the wound bed:
metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine); iron III reductants; or
agents for the adjustment of pH in the wound exudate, such as base or acid scavengers and/or ion exchangers, or other species, which may be non-labile, insoluble and/or immobilised) species, such as ScavengePore® phenethyl morpholine (Aldrich).

It will be appropriate to design and run the apparatus with this type of cleansing means either as a 'circulating system', or in the form of a 'reversing system', since the fluid passing through the cleansing means at least once in the reverse direction would not return these materials into the wound.)

An example of such systems is shown inter alia in FIGS. 1, 6 and 7 (reversing system) and 2, 8 and 9 (circulating system) hereinafter.

A second, selectively permeable integer, again suitably a flat sheet or membrane of a polymeric material may be required to form part of a distal chamber wall in the flowpath in any appropriate part of the apparatus to retain materials that are deleterious to wound healing and antagonists or other active materials in the chamber.

A particular advantage of this form of the system, is that where a material that can remove materials deleterious to wound healing from wound exudate is (cyto)toxic or bioincompatible, or not inert to any components that are beneficial in promoting wound healing, the system does not allow any significant amounts of it to pass into the wound.

In two-phase systems, the chamber contains a cleansing fluid, most usually a fluid (dialysate) phase. The latter is separated from the wound exudate by means of a permeable integer.

At least one fluid is moved through the means for fluid cleansing by at least one device, in particular across the permeable integer, for example the polymer film, sheet or membrane.

This promotes the passage of relatively high concentrations of solutes or disperse phase species, including deleterious materials, from the wound exudate into the cleansing fluid and the chamber and optionally the system in which the cleansing fluid recirculates. Such systems are described further below.

The fluid that is moved through the means for fluid cleansing by the device for moving fluid is
a) the cleansing fluid or
b) the wound exudate optionally mixed with irrigant, or
c) both.

Examples of such systems are shown in FIGS. 12 and 13 hereinafter, in which FIGS. 12*a* and 13 show such a system, a dialysis unit, in which only the cleansing fluid separated from the wound exudate is the moving fluid.

FIG. 12*b* shows such a system, a dialysis unit, in which the cleansing fluid and the wound exudate optionally with irrigant are the moving fluids.

The cleansing fluid is less usually static as in FIG. 4, as this may not be a system with sufficient (dynamic) surface area to remove materials deleterious to wound healing from wound exudate at a practical rate.

Typical dialysate flow rates in a dialytic means for fluid cleansing in the present apparatus for aspirating, irrigating and/or cleansing wounds are those used in the conventional type of two-phase system, such as a dialysis unit for systemic therapy.

The integer may be a film, sheet or membrane, often of the same type, and of the same (generally uniform) thickness, as those used in conventional two-phase system, such as a dialysis unit for systemic therapy.

As noted above, the film, sheet or membrane may be substantially flat, but, especially where the cleansing fluid circulates, it may more suitably be in the form of pipes, tubes or tubules in an array.

The surface area of any such film, sheet or membrane may be suitably be no less than 50 mm$^2$, such 100 to 1000000 mm$^2$, e.g. 500 to 25000 mm$^2$ If both fluids move it may be in co- or preferably counter-current direction.

Again, materials deleterious to wound healing are removed into the dialysate, and the cleansed fluid, still containing materials that are beneficial in promoting wound healing, remains or is returned by recirculation to the wound.

Examples of these deleterious materials as above include oxidants, such as free radicals, e.g. peroxide and superoxide; iron II and iron III; all involved in oxidative stress on the wound bed;
proteases, such as serine proteases, e.g. elastase and thrombin; cysteine proteases, matrix metalloproteases, e.g. collagenase; and carboxyl (acid) proteases;

endotoxins, such as lipopolysaccharides;

autoinducer signalling molecules, such as homoserine lactone derivatives, e.g. oxo-alkyl derivatives;

inhibitors of angiogenesis such as thrombospondin-1 (TSP-1), plasminogen activator inhibitor, or angiostatin (plasminogen fragment)

pro-inflammatory cytokines such as tumour necrosis factor alpha (TNFα) and interleukin 1 beta (IL-1β); and inflammatories, such as lipopolysaccharides, and e.g. histamine; and basic or acidic species which adversely affect the pH in the wound exudate, such as protons.

Examples of suitable materials for the film, sheet or membrane (typically in the form of conformable hollow bodies defined by the film, sheet or membrane, such as the structures described hereinbefore) include natural and synthetic polymeric materials.

The membrane may be of one or more hydrophilic polymeric materials, such as a cellulose derivative, e.g. regenerated cellulose, a cellulose mono-, di- or tri-esters, such as cellulose mono-, di- or tri-acetate, benzyl cellulose and Hemophan, and mixtures thereof.

Examples of other materials include hydrophobic materials, such as aromatic polysulphones, polyethersulphones, polyetherether-sulphones, polyketones, polyetherketones and polyetherether-ketones, and sulphonated derivatives thereof, and mixtures thereof.

Examples of other materials include hydrophobic materials, such as polyesters, such as polycarbonates and polyamides, e.g. 6-6 and 6-10; polyacrylates, including, e.g. poly(methyl methacrylate), polyacrylonitrile and copolymers thereof, for example acrylonitrile-sodium metallosulphonate copolymers; and poly(vinylidene chloride).

Suitable materials for the present membranes include thermoplastic polyolefins, such as polyethylene e.g. high-density polyethylene, polypropylene, copolymers thereof, for example with vinyl acetate and polyvinyl alcohol, and mixtures thereof.

The dialysis membrane should have a molecular weight cut off (MWCO) chosen to allow selective perfusion of species deleterious to wound healing that have been targeted for removal from the wound. For example, perfusion of the serine protease elastase (molecular weight 25900 Dalton) would require a membrane with MWCO>25900 Dalton. The MWCO threshold can be varied to suit each application between 1 and 3000000 Dalton.

Preferably, the MWCO should be as close as possible to this weight to exclude interference by larger competitor species.

For example, such a membrane with MWCO>25900 Dalton does not allow any significant amounts of the antagonist to elastase, alpha-1-antitrypsin (AAT) (molecular weight 54000 Dalton), which occurs naturally in wounds, to diffuse freely out of the wound fluid into the dialysate. The inhibitor, which is beneficial in promoting chronic wound healing, remains in contact with the wound bed, and can act beneficially on it, whilst the elastase that is deleterious to wound healing is removed.

Such use of the present apparatus is, e.g. favourable to the wound healing process in chronic wounds, such as diabetic foot ulcers, and especially decubitus pressure ulcers.

As noted hereinafter, antagonists, for example degrading enzymes, or sequestrating agents for elastase on the dialysate side of the membrane, may be used to enhance the removal of this protease from wound exudate.

A less conventional type of two-phase system (see above) may be used as the means for fluid cleansing. In this type, the dialysis polymer film, sheet or membrane is not an integer selectively permeable to materials deleterious to wound healing, such as proteases, such as serine proteases, e.g. elastase, and thrombin; cysteine proteases; matrix metalloproteases, e.g. collagenase; and carboxyl (acid) proteases;

endotoxins, such as lipopolysaccharides;

inhibitors of angiogenesis such as thrombospondin-1 (TSP-1), plasminogen activator inhibitor, or angiostatin (plasminogen fragment)

pro-inflammatory cytokines such as tumour necrosis factor alpha (TNFα) and interleukin 1 beta (IL-1β);

oxidants, such as free radicals, e.g., e.g. peroxide and superoxide; and metal ions, e.g. iron II and iron III; all involved in oxidative stress on the wound bed; and basic or acidic species which adversely affect the pH in the wound exudate, such as protons.

It will however also permit components of the exudate from a wound and/or irrigant fluid that may be larger or smaller molecules, but are beneficially involved in wound healing to pass into and through it.

In the dialysate, or preferably in one or more solid structural integers with at least one surface in contact with the dialysate, in the means for fluid cleansing, there are one or more materials that can remove materials deleterious to wound healing from wound exudate, by being antagonists to such species, for example enzymes or others, such as protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide; cysteine protease inhibitors; matrix metalloprotease inhibitors; and carboxyl (acid) protease inhibitors;

binders and/or degraders, such as anti-inflammatory materials to bind or destroy lipopolysaccharides, e.g. peptidomimetics;

anti-oxidants, such as 3-hydroxytyramine (dopamine), ascorbic acid (vitamin C), vitamin E and glutathione, and stable derivatives thereof, and mixtures thereof; to relieve oxidative stress on the wound bed;

metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine); iron III reductants; and agents for the adjustment of pH in the wound exudate, such as base or acid scavengers and/or ion exchangers, or other species, which may be non-labile, insoluble and/or immobilised) species, such as ScavengePore® phenethyl morpholine (Aldrich).

They further include peptides (including cytokines, e.g. bacterial cytokines, such as α-amino-γ-butyrolactone and L-homocarnosine); and sacrificial redox materials that are potentially or actually beneficial in promoting wound healing, such as iron III reductants; and/or regeneratable materials of this type, such as glutathione redox systems; and other physiologically active components.

In use of the two-phase system dialysis unit, of this less conventional type, a broad spectrum of species will usually pass into the dialysate from the exudate.

Some (mainly ionic) species will pass from the dialysate into the irrigant and/or wound exudate through the dialysis polymer film, sheet or membrane that is not very selectively permeable to materials deleterious to wound healing.

The components of the exudate from a wound and/or irrigant fluid will diffuse freely to and fro through it.

A steady state concentration equilibrium is eventually set up between the dialysate and the irrigant and/or wound exudate, which is 'topped up' from the wound dressing.

Circulating wound fluid aids in the quicker attainment of this equilibrium of materials beneficial in promoting wound healing.

It also returns them to the site where they can be potentially of most benefit, i.e. the wound bed.

The target materials deleterious to wound healing also pass into the dialysate from the exudate through the dialysis polymer film, sheet or membrane that is not very selectively permeable to materials deleterious to wound healing.

Unlike the other components of the exudate from a wound and/or irrigant fluid, the target materials deleterious to wound healing come into contact with the dialysate, or preferably with one or more solid structural integers with at least one surface in the dialysate, and are removed by the appropriate antagonists, binders and/or degraders, chelators and/or ion exchangers and redox agents, etc. The cleansed fluid, still containing some materials that are beneficial in promoting wound healing, is returned to the wound.

Unlike the other components of the exudate from a wound and/or irrigant fluid the target materials are constantly removed from the dialysate, very little of these species will pass from the dialysate into the irrigant and/or wound exudate, and a steady state concentration equilibrium is not set up, even if the species are constantly 'topped up' from the wound dressing.

It is believed that circulating one or both fluids aids in removal from recirculation of the materials deleterious to wound healing from wound exudate, whilst retaining materials that are beneficial in promoting wound healing in contact with the wound.

A particular advantage of this form of the two-phase system, is that where a material that can remove materials deleterious to wound healing from wound exudate is (cyto) toxic or bioincompatible, or not inert to any components that are beneficial in promoting wound healing, the system does not allow any significant amounts of antagonist to diffuse freely out of the dialysate into the wound fluid. The active material can act beneficially on the fluid however. The film sheet or membrane is preferably a dialysis membrane of molecular weight cut off (MWCO) (as conventionally defined) chosen to allow perfusion of species targeted for sequestration or destruction.

For example, sequestration of the serine protease elastase (molecular weight 25900 Dalton) would require a membrane with MWCO>25900 Dalton.

The MWCO threshold can be varied to suit each application between 1 and 3 000 000 Dalton. Preferably, the MWCO should be as close as possible to this weight to exclude sequestering interference by larger competitor species.

It will be seen that in many of the embodiments of the apparatus of this first aspect of the present invention for cleansing wounds, the irrigant and/or wound exudate and/or the cleansing fluid passes from the wound dressing and is returned via a return path to it, through or under the backing layer with a wound-facing face which is capable of forming a relatively fluid-tight seal or closure over a wound.

Each return path will require
at least one inlet pipe for connection to a fluid return tube, which passes through the wound-facing face of the backing layer, and
at least one outlet pipe for connection to a fluid offtake tube, which passes through the wound-facing face of the backing layer,
the point at which the or each inlet pipe and the or each outlet pipe passes through or under the wound-facing face forming a relatively fluid-tight seal or closure over the wound.

Where any pipe is described in connection with the operation of the apparatus as being connected or for connection to a (mating end of a) tube, the pipe and the tube may form a single integer.

Where the mode of running the present apparatus is in the form of a 'reversing system', the at least one inlet pipe and the at least one outlet pipe, and the at least one fluid supply tube and the at least one outlet pipe, may respectively be the same integer.

This is often in a 'multiple-pass system' for irrigant and/or wound exudate where this fluid passes from the wound dressing and is returned to the wound, in both cases via the cleansing means, e.g. under the action of the movement of a reciprocating pump, such as a syringe or piston pump.

The or each inlet pipe or outlet pipe may have the form of an aperture, such as a funnel, hole, opening, orifice, luer, slot or port for connection as a female member respectively to a mating end of a fluid return tube or a fluid offtake tube (optionally or as necessary via means for forming a tube, pipe or hose, or nozzle, as a male member.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound).

This is usually around each relevant tube, pipe or hose, or nozzle, hole, opening, orifice, luer, slot or port for connection to a mating end of a fluid return tube or fluid offtake tube.

Alternatively or additionally, where appropriate the backing layer may have a stiff flange or lip extending around the proximal face of the backing layer to stiffen, reinforce or otherwise strengthen the backing layer.

Both the single-phase system, such as an ultrafiltration unit, and two-phase system, such as a dialysis unit, may be in modular form that is relatively easily demountable from the apparatus of the invention.

Each return flow path (whether in a single-phase system or a two-phase system, such as an dialysis unit) requires a means for moving fluid.

Suitable means will be apparent to the skilled person, but the following types of small pump may be used as desired:
small reciprocating pumps, such as:
diaphragm pumps—where pulsations of one or two flexible diaphragms displace liquid while check valves control the direction of the fluid flow.
syringe and piston
pumps—where pistons pump fluids optionally through check valves, in particular for variable and/or reversible positive and/or negative pressure on the wound bed and for closed single-phase reversing system, in which the wound exudate and/or irrigant passes to and fro through the cleansing means.

small rotary pumps, such as:

rotary vane pumps—with rotating vaned disk attached to a drive shaft moving fluid without pulsation as it spins. The outlet can be restricted without damaging the pump.

peristaltic pumps—with peripheral rollers on rotor arms acting on a flexible fluid circulation tube to urge fluid current flow in the tube in the direction of the rotor, in particular for a dialysate phase in a multiple-phase circulating system, in which it passes in only one direction.

The type and/or capacity of the device will be largely determined by the appropriate or desired fluid volume flow rate of irrigant and/or wound exudate from the wound for optimum performance of the wound healing process, and by factors such as portability, power consumption and isolation from contamination.

Such a device may also suitably be one that is capable of pulsed, continuous, variable, reversible and/or automated and/or programmable fluid movement. It may in particular be a pump of any of these types.

The main function of the invention, i.e. an apparatus, that is advantageously portable, for irrigating and/or cleansing wounds will largely determine the main function of the pump, i.e. a moving device for moving fluid, e.g. (chronic) wound exudate, through the cleansing means, rather than for aspirating or pressurising wounds that are being cleansed.

It may however be used to apply a positive or negative pressure of up to 50% atm., more usually up to 15% atm., to the wound, which may be pulsed, continuous, variable, reversible, automated and/or programmable, as for fluid movement.

A fluid-tight seal or closure of the wound dressing around the periphery of the backing layer then becomes more crucial, if wound cleansing is to be applied in this way.

The device is favourably a small peristaltic pump or diaphragm pump, e.g. preferably a miniature portable diaphragm or peristaltic pump. These are preferred types of pump, in order in particular to reduce or eliminate contact of internal surfaces and moving parts of the pump with (chronic) wound exudate, and for ease of cleaning.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as an electromechanical oscillator, a piezoelectric transducer, a core of a solenoid or a ferromagnetic integer and coil in which the direction of current flow alternates, a rotary cam and follower, and so on In one embodiment of the apparatus of this first aspect of the present invention for cleansing wounds with a two-phase system, such as one with a dialysis unit, no fluid passes from the wound dressing or is returned via a return path to it, through the backing layer.

It therefore does not require any inlet pipe for connection to a fluid return tube or any outlet pipe for connection to a fluid offtake tube, which passes through the wound-facing face of the backing layer.

In such an embodiment, the prime purpose of the moving device is to move the cleansing fluid. In such an embodiment, amongst suitable devices are:

Suitable examples of such a dressing include, e.g. those making use of rotary impellers, such as: vane impellers, with rotating vaned disk attached to a drive shaft, propellers on a drive shaft, etc.

Such devices may be integral with the dressing. It will be seen that the corresponding apparatus disadvantageously has a need to ensure a fluid-tight seal or closure of the chamber around any part of the moving device where it passes through the chamber wall or wound dressing. They may (disadvantageously) not be portable.

The possibility of using this type of wound dressing may be largely determined by the ability to achieve such a relatively fluid-tight seal or closure. It may be desirable that no part of the moving device pass through the chamber wall or wound dressing.

They may be separate structures, capable of interacting as appropriate for the purpose of moving cleansing fluid along a desired flow path across the selectively permeable integer, effectively in a 'multiple-pass system' within the interior of the chamber.

The moving device may drive the cleansing fluid inside the chamber remotely to set it in motion.

Such an embodiment of the apparatus advantageously enables a tight seal or closure over the wound, and no part of the moving device need pass through the chamber wall or wound dressing.

This avoids the need to ensure a fluid-tight seal or closure of the chamber around it.

The chamber may thus, e.g. be provided in a form with at least one magnetic follower enclosed within it and acted upon by a magnetic stirrer to impel the cleansing fluid. The magnetic stirrer to impel the cleansing fluid may be mounted on, e.g. releasably attached to the other components of the dressing, in particular the backing layer, e.g. with a Velcro™ attachment, an adhesive film (e.g. of pressure-sensitive adhesive) or elastic or non-elastic straps, bands, ties, bandages, e.g. compression bandages, sheets or covers, or be a push, snap or twist-lock fit with it/tem.

It may be mounted, e.g. centrally, on the backing layer above a circular or concentric toroidal hollow body that effectively forms an annular chamber provided with at least one magnetic follower within it. In use, the magnetic stirrer impels the magnetic follower enclosed within respectively the circular or the annular chamber to cause the wound cleansing fluid to circulate.

The film, sheet or membrane is often selectively permeable, contains the cleansing fluid, and should have the right resilience against the pulsing pressure to allow significant compression or decompression of the chamber to recirculate the wound cleansing fluid through it.

All such remote devices may be integral with or permanently attached to the dressing, in particular the backing layer, with an adhesive film, for example, or by heat-sealing.

These components may be releasably attached, e.g. by a Velcro™ attachment, with an adhesive film (e.g. with pressure-sensitive adhesive) or with elastic and non-elastic straps, bands, ties, bandages, e.g. compression bandages, sheets or covers.

Another such a device may be provided in the form of at least one ball or sphere, e.g. a solid metal ball or sphere.

This sets the cleansing fluid is in motion in contact with the surface of the integer that is selectively permeable to materials in the wound exudate under the action of the bodily movement of the patient.

Alternatively, the top of a compressible chamber may be provided with a trackway, around which the patient may run his or her fingers to move the fluid around the chamber.

In practice, even from a wound in a highly exuding state, such a rate of exudate flow is only of the order of up to 75 microlitres/$cm^2$/hr (where $cm^2$ refers to the wound area), and the fluid can be highly mobile (owing to the proteases present).

Exudate levels drop and the consistency of wound exudate changes, e.g. to a higher viscosity liquid, as the wound heals, e.g. to a level for the same wound that equates to 12.5-25 microlitres/cm$^2$/hr.

Where materials deleterious to wound healing are removed by a two-phase system (See below.), such as a dialysis unit, fluid is also potentially lost to the system through the means for fluid cleansing.

This may occur, e.g. through a dialysis polymer film, sheet or membrane which is also permeable to water, in addition to materials deleterious to wound healing.

The balance of fluid in recirculation may thus further decrease. It may be desired to adjust the volume of the irrigant and/or wound exudate and hence to minimise this undesired loss.

If the consistency of wound exudate changes, e.g. to a higher viscosity liquid, as the wound heals, it may be desired to adjust the volume of the irrigant and/or wound exudate and hence to adjust the viscosity of the liquid, e.g. to a level that equates to the initial level.

As noted above, the apparatus of this first aspect of the present invention for cleansing wounds may be used with the wound space at atmospheric pressure or at a positive or negative pressure of up to 50% atm., more usually up to 15% atm. applied to the wound.

A fluid may be added to or removed from the wound space before and/or during wound therapy as may be desired to adjust the volume of the irrigant and/or wound exudate and/or to adjust the neutral, positive or negative pressure on the wound.

Thus, the volume of irrigant and/or wound exudate from the wound may be increased by continuing addition of irrigant to the wound space. A positive pressure may be applied to the wound by for example flooding it with a desired amount of irrigant before the dressing is applied to it and/or by continuing addition of irrigant to the wound during the run. A negative pressure may be applied to the wound by means of fluid removal from the wound, for example with a small pump.

This may be achieved in all cases by passage of the relevant fluid freely to and fro through a fluid regulator, such as a valve or other control device, e.g. a valve that is turned to switch between open and closed, that is mounted in a pipe or tube that passes through or under the backing layer.

For example, if exudate build-up under the backing layer becomes excessive during use, a bleed valve may be opened and excess fluid vented off, e.g. to a waste reservoir, and any excess pressure relieved.

Equally, any loss from any fluid from the wound may be adjusted, or a positive pressure (i.e. above-atmospheric pressure) may be applied to the wound bed by means of an irrigant which passes through a similar input regulator, such as a valve or other control device, e.g. a valve that is turned to switch between on and off, through or under the backing layer to the wound bed.

A negative pressure may be conveniently applied to the wound bed by means of fluid removal from the wound, for example with a small pump, through a similar vacuum regulator, such as a valve or other control device, e.g. a valve that is turned to closure once the vacuum has been applied, before disconnection of the vacuum source.

Alternatively or additionally, where appropriate the backing layer may have a regulator such as an injection septum, through which the desired amount of the relevant fluid, such as irrigant, may be removed from or supplied to the wound, for example with a small syringe or like pump to achieve the desired effect.

Equally, the balance in any cleansing fluid may be adjusted by means for bleeding or supplying fluid to the relevant flowpath. The means for bleeding or supplying fluid to the relevant flowpath may be situated in any appropriate part of the apparatus that is in contact with the cleansing fluid.

The means for bleeding or supplying fluid to the flowpath may be a regulator, such as a valve or other control device, e.g. a valve that is turned to switch between bleed and closure, for bleeding fluids from the apparatus, e.g. to a waste reservoir, such as a collection bag, or to switch between supply and closure, for supplying fluids to the apparatus.

Alternatively or additionally, where appropriate the flowpath may have a regulator such as an injection septum, through which the desired amount of the relevant fluid cleanser may be removed from or supplied to the flowpath, e.g. with a small syringe or like pump to achieve the desired effect.

The inlet and/or outlet pipes, the fluid return tube and the fluid offtake tube, etc. where present may be of conventional type, e.g. of elliptical or circular cross-section, and may suitably have a uniform cylindrical bore, channel, conduit or passage throughout their length.

Depending on the desired fluid volume flow rate of irrigant and/or wound exudate from the wound, and the desired amount in recirculation, suitably the largest cross-dimension of the bore may be up to 10 mm for large torso wounds, and up to 2 mm for limb wounds.

The tube walls should suitably thick enough to withstand any positive or negative pressure on them.

This is in particular the case if the volume of irrigant and/or wound exudate from the wound in recirculation is increased by continuing addition to it of wound exudate, and/or fluid passing from a cleansing fluid through a selectively permeable integer, for example the polymer film, sheet or membrane of a two-phase system, such as an dialysis unit. However, as noted above with regard to pumps, the prime purpose of such tubes is to convey irrigant and exudate through the length of the apparatus flow path, rather than to act as pressure vessels. The tube walls may suitably be at least 25 micron thick.

The whole length of the apparatus for aspirating, irrigating and/or cleansing wounds should be microbe-impermeable once the wound dressing is over the wound in use.

It is desirable that the wound dressing and the interior of the apparatus for aspirating, irrigating and/or cleansing wounds of the present invention is sterile.

The fluid may be sterilised in the system in which the fluid moves, including the means for fluid cleansing, by ultraviolet, gamma or electron beam irradiation. This way, in particular reduces or eliminates contact of internal surfaces and the fluid with any sterilising agent.

Examples of other methods of sterilisation of the fluid also include e.g. the use of ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide;

although the latter involve contact of internal surfaces and the fluid with the sterilising agent.

It may be desirable that the interior of the wound dressing, the rest of the system in which the fluid recirculates, and/or the wound bed, even for a wound in a highly exuding state, are kept sterile, or that at least naturally occurring microbial growth is inhibited.

It is also desirable to provide a system in which physiologically active components of the exudate that are beneficial to wound healing are not removed before or after the application of fluid cleansing, e.g. by the passive deposition of materials that are beneficial in promoting wound healing, such as proteins, e.g. growth factors.

This may occur at any point in the system that is in contact with such physiologically active components of the exudate that are beneficial to wound healing.

Often this will occur at any point in the system that is in contact with the exudate, usually in a single-phase system, but it may occur in the second fluid (dialysate) phase in a multiple-phase system where materials in the wound exudate that are potentially beneficial to wound healing diffuse freely into that phase in use of the apparatus.

The deposition of materials that are beneficial in promoting wound healing may be combated by using a repellent coating at any point or on any integer in direct contact with the relevant fluid.

Examples of coating materials for surfaces over which the circulating fluid passes include
anticoagulants, such as heparin, and
high surface tension materials, such as PTFE, and polyamides,
which are useful for growth factors, enzymes and other proteins and derivatives.

In all embodiments of the apparatus the type and material of any tubes throughout the apparatus of the invention for irrigating and/or cleansing wounds will be largely determined by their function.

To be suitable for use, in particular on chronic timescales, the material should be non-toxic and biocompatible, inert to any active components, as appropriate of the irrigant and/or wound exudate and of any dialysate. It should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials include synthetic polymeric materials, such as polyolefins, such as polyethylene, e.g. high-density polyethylene and polypropylene.

Suitable materials for the present purpose also include copolymers thereof, for example with vinyl acetate and mixtures thereof. Suitable materials for the present purpose further include medical grade poly(vinyl chloride).

For the purposes of fluid cleansing in the apparatus of the present invention, both the single-phase system, such as an ultrafiltration unit, and two-phase system, such as a dialysis unit, may have captive (non-labile, insoluble and/or immobilised) species such as the following, bound to an insoluble and/or immobilised) substrate over and/or through which the irrigant and/or wound exudate from, the wound dressing passes in turn to the fluid return tube(s):
antioxidants and free radical scavengers, such as 3-hydroxytyramine (dopamine), ascorbic acid (vitamin C), vitamin E and glutathione, and stable derivatives thereof, and mixtures thereof; to relieve oxidative stress on the wound bed;
metal ion chelators and/or ion exchangers, such as transition metal ion chelators, such as iron III chelators (Fe III is involved in oxidative stress on the wound bed.), such as desferrioxamine (DFO), 3-hydroxytyramine (dopamine); iron III reductants;
protease inhibitors, such as TIMPs and alpha 1-antitrypsin (AAT); serine protease inhibitors, such as 4-(2-aminoethyl)-benzene sulphonyl fluoride (AEBSF, PefaBloc) and N-α-p-tosyl-L-lysine chloro-methyl ketone (TLCK) and ε-aminocaproyl-p-chlorobenzylamide; cysteine protease inhibitors; matrix metalloprotease inhibitors; and carboxyl (acid) protease inhibitors;
sacrificial redox materials that are potentially or actually beneficial in promoting wound healing, by the removal of materials that trigger the expression into wound exudate of redox-sensitive genes that are deleterious to wound healing; autoinducer signalling molecule degraders, which may be enzymes; and
anti-inflammatory materials to bind or destroy lipopolysaccharides, e.g. peptidomimetics;
agents for the adjustment of pH in the wound exudate, such as base or acid scavengers and/or ion exchangers, or other species, which may be non-labile, insoluble and/or immobilised) species, such as ScavengePore® phenethyl morpholine (Aldrich).

Other physiologically active components of the exudate that are deleterious to wound healing may be removed in this way.

These may be removed with suitable chelators and/or ion exchangers, degraders, which may be enzymes, or other species.

The following types of functionalised substrate has sites on its surface that are capable of removing materials deleterious to wound healing on passing the circulating fluid from the wound over them:
heterogeneous resins, for example silica-supported reagents such as:
metal scavengers,
3-(diethylenetriamino)propyl-functionalised silica gel
2-(4-(ethylenediamino)benzene)ethyl-functionalised silica gel
3-(mercapto)propyl-functionalised silica gel
3-(1-thioureido)propyl-functionalised silica gel
triamine tetraacetate-functionalised silica gel
or electrophilic scavengers,
4-carboxybutyl-functionalised silica gel
4-ethyl benzenesulfonyl chloride-functionalised silica gel
propionyl chloride-functionalised silica gel
3-(isocyano)propyl-functionalised silica gel
3-(thiocyano)propyl-functionalised silica gel
3-(2-succinic anhydride)propyl-functionalised silica gel
3-(maleimido)propyl-functionalised silica gel
or nucleophilic scavengers,
3-aminopropyl-functionalised silica gel
3-(ethylenediamino)-functionalised silica gel
2-(4-(ethylenediamino)propyl-functionalised silica gel
3-(diethylenetriamino)propyl-functionalised silica gel
4-ethyl-benzenesulfonamide-functionalised silica gel
2-(4-toluenesulfonyl hydrazino)ethyl-functionalised silica gel
3-(mercapto)propyl-functionalised silica gel
dimethylsiloxy-functionalised silica gel
or base or acid scavengers,
3-(dimethylamino)propyl-functionalised silica gel
3-(1,3,4,6,7,8-hexahydro-2H-pyrimido-[1,2-α]pyrimidino) propyl-functionalised silica gel
3-(1-imidazol-1-yl)propyl-functionalised silica gel
3-(1-morpholino)propyl-functionalised silica gel
3-(1-piperazino)propyl-functionalised silica gel 3-(1-piperidino)propyl-functionalised silica gel
3-(4,4'-trimethyldipiperidino)propyl-functionalised silica gel
2-(2-pyridyl)ethyl-functionalised silica gel
3-(trimethylammonium)propyl-functionalised silica gel or the reagents,
3-(1-cyclohexylcarbodiimido)propyl-functionalised silica gel
TEMPO-functionalised silica gel
2-(diphenylphosphino)ethyl-functionalised silica gel
2-(3,4-cyclohexyldiol)propyl-functionalised silica gel
3-(glycidoxy)propyl-functionalised silica gel
2-(3,4-epoxycyclohexyl)propyl-functionalised silica gel
1-(allyl)methyl-functionalised silica gel
4-bromopropyl-functionalised silica gel
4-bromophenyl-functionalised silica gel
3-chloropropyl-functionalised silica gel
4-benzyl chloride-functionalised silica gel
2-(carbomethoxy)propyl-functionalised silica gel
3-(4-nitrobenzamido)propyl-functionalised silica gel
3-(ureido)propyl-functionalised silica gel
or any combinations of the above.

The use of such captive (non-labile, insoluble and/or immobilised) species, such as the foregoing, bound to an insoluble and immobilised) substrate over and/or through which the irrigant and/or wound exudate from, the wound dressing passes has been described hereinbefore as suitable for the means for fluid cleansing.

However, they may additionally, where appropriate, be used in any part of the apparatus that is in contact with the irrigant and/or wound exudate, but often within the dressing, for removal of materials deleterious to wound healing from wound.

In a second aspect of the present invention there is provided a method of treating wounds to promote wound healing using the apparatus for cleansing wounds of the present invention.

BRIEF DESCRIPTION OF THE DRAWINGS

The present invention will now be described by way of example only with reference to the accompanying drawings in which.

DETAILED DESCRIPTION OF THE PREFERRED EMBODIMENT

Figure 1:
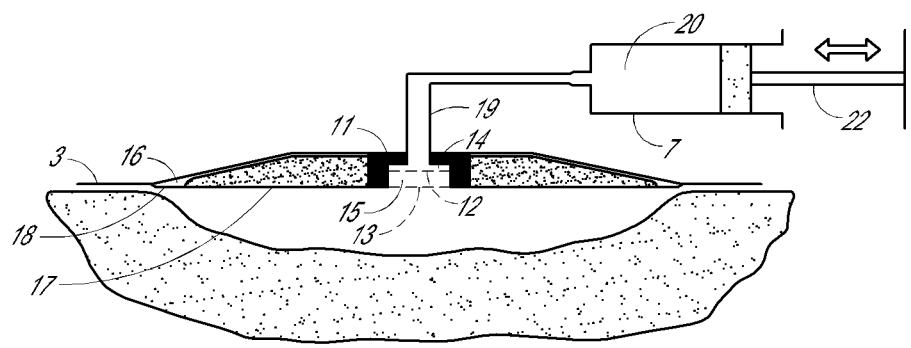
FIG. 1 is a cross-sectional view of an apparatus for cleansing a wound according to the first aspect of the present invention, the apparatus with a single-phase means for wound exudate cleansing, and a reversing system, in which the wound exudate and optionally irrigant passes through the cleansing means one or more times at least once in opposing directions.

Referring to FIGS. 1 to 10 and 14, the apparatus (1) for cleansing wounds comprises
a conformable wound dressing (2), having
a backing layer (3) which is capable of forming a relatively fluid-tight seal or closure over a wound and bears an adhesive film, to attach it to the skin sufficiently to hold the wound dressing (2) in place;
a cleansing means (4) for selectively removing materials that are deleterious to wound healing from wound exudate, which means is under the backing layer (3) and sits in the underlying wound in use; and
a moving device (7) for moving fluid through the cleansing means.

Optional means for bleeding or supplying fluid to the cleansing means (4) or to exudate under the backing layer, e.g. a regulator, such as a valve are omitted in most of the Figures.

In FIG. 1, a reversing system is shown (wound exudate passes through the cleansing means at least once in opposing directions).

The microbe-impermeable film backing layer (3) bears a centrally attached proximally projecting recessed boss (11).

A porous film (12) and a permeable membrane (13) mounted in the recess (14) of the boss (11) define a cleansing chamber (15), which contains a solid particulate (not shown) for sequestering deleterious materials from, but initially separated from the wound exudate. These integers form the cleansing means (4).

An annular chamber (16) about the boss (11) is defined by a fluid-impermeable film (17) that extends between and is attached to the boss (11) and the underside of the backing layer (3). It is filled with a flexibly resilient foam (18)

An inlet and outlet pipe (19) passes centrally through the boss (11) and communicates between the interior of the boss (11) and a syringe barrel (20), which is part of a syringe moving device (7).

In use, movement of the syringe plunger (22) sucks and forces wound exudate to and fro through the cleansing means (4).

Figure 2:
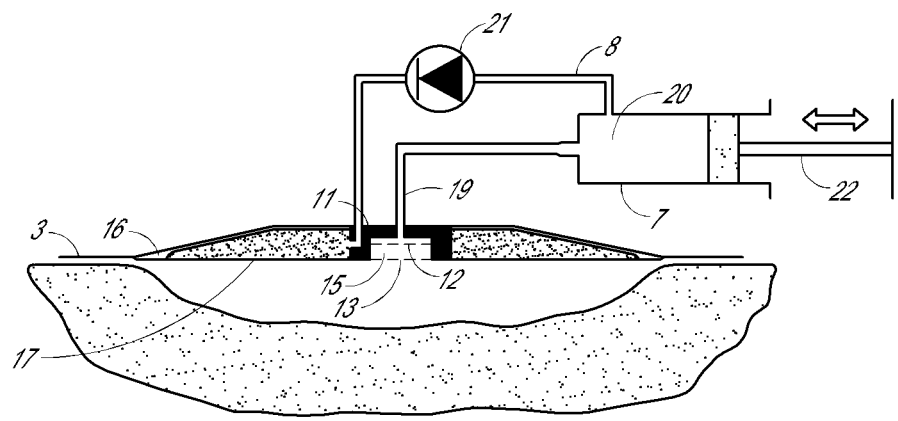
FIG. 2 is a cross-sectional view of an apparatus for cleansing a wound according to the first aspect of the present invention, the apparatus with a single-phase means for wound exudate cleansing, a circulating system in which it/they pass in only one direction, and a reversing system, in which the wound exudate and optionally irrigant passes through the cleansing means one or more times at least once in opposing directions.

The apparatus (1) in FIG. 2 may be operated as a circulating system or as both a circulating system and as a reversing system.

It is similar in construction to FIG. 1, but differs mainly in that an inlet pipe return loop (19) passes in a bend through the boss (11) and communicates between the interior of the chamber (16) and the syringe barrel (20) via a non-return valve (21), the resistance of which to flow is low relative to the resistance of the cleansing means (4). Means for bleeding fluid from the chamber (16), such as a valve, is omitted from FIG. 2.

In use, the plunger (22) of the syringe moving device (7) is withdrawn to suck wound exudate into the cleansing means (4), which sequesters deleterious materials from the wound exudate.

The plunger (22) of the syringe moving device (7) is then returned to force cleansed wound exudate through the valve (21) into the annular chamber (16), and thence through the porous film (17) back into the wound.

A proportion of cleansed wound exudate is also pushed back through the cleansing means (4) at each return stroke of the syringe plunger. The proportion will depend largely on the position of the return loop (19) on the syringe barrel. The amount pumped to the annular chamber (16) will decrease the further from the proximal end of the syringe the return loop links to the syringe barrel, as the plunger cuts off the return loop (19) in the later part of the return stroke.

Depending largely on the type of cleansing means that is employed in this embodiment of the apparatus of the present invention, the resistance of the valve (21) relative to the resistance of the cleansing means (4) may also affect the proportion through the chamber (16) and through the porous film (17).

Excess pressure in the chamber (16), e.g. from wound exudate from a wound in a highly exuding state, may be relieved by a bleed valve, if fitted.

Figure 3:
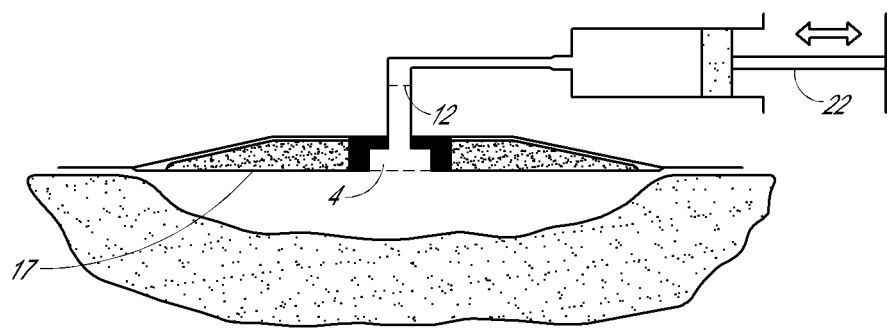
FIG. 3 is a cross-sectional view of an apparatus for cleansing a wound according to the first aspect of the present invention, the apparatus with a single-phase means for wound exudate cleansing, and a reversing system, in which the wound exudate and optionally irrigant passes through the cleansing means one or more times at least once in opposing directions.

The apparatus (1) in FIG. 3 differs mainly from that in FIG. 2 in the position of the porous film (12) in the flow path.

The mode of use is the same: movement of the syringe plunger (22) sucks and forces wound exudate to and from through the cleansing means (4).

Figure 4A:
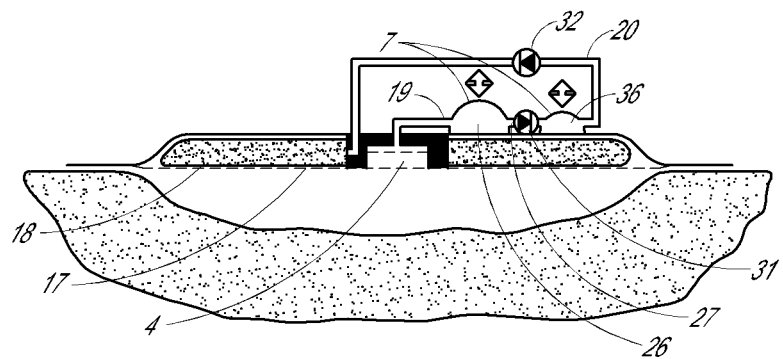
FIG. 4a is a cross-sectional view of an apparatus for cleansing a wound according to the first aspect of the present invention, the apparatus with a single-phase means for wound exudate cleansing, and a circulating system, in which it/they pass in only one direction.
Figure 4B:
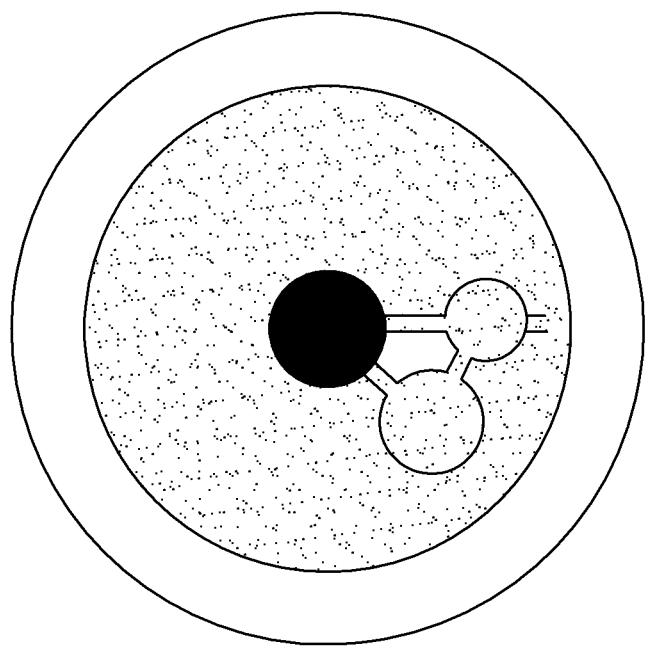
FIG. 4b is a top view of an apparatus for cleaning a wound according to the first aspect of the present invention, the apparatus with a single-phase means for wound exudate cleansing, and a circulating system, in which it/they pass in only one direction.

The apparatus (1) in FIG. 4 differs from that in FIG. 2 in the moving device (7).

This is a press-button pump in place of a syringe. The pump (7) is mounted on the distal face of the backing layer (3).

It comprises a resiliently compressible intake chamber (26), connected by an outlet pipe (19) to the cleansing means (4) and by a transfer tube (27) via a low resistance first non-return valve (31) to a resiliently compressible output chamber (36), connected via an inlet pipe (20) and a low resistance second non-return valve (32) to the interior of the chamber (16).

In use, the intake chamber (26) is manually compressed and released, its return to its original configuration causing wound exudate to be drawn through the cleansing means (4).

The output chamber (36) is then manually compressed and released, its return to its original configuration causing cleansed wound exudate to be drawn through the first non-return valve (31) from the intake chamber (26).

The intake chamber (26) is then manually compressed again and released, its compression causing cleansed wound exudate to be pumped into the output chamber (36) through the first non-return valve (31) from the intake chamber (26), and its return to its original configuration causing wound exudate to be drawn through the cleansing means (4).

The output chamber (36) is then manually compressed again and released, its compression causing cleansed wound exudate to be pumped into the chamber (16) through the second non-return valve (32) from the output chamber (36), and its return to its original configuration causing cleansed wound exudate to be drawn through the intake chamber (26).

The cycle is repeated as long as desired, and from the second cycle onwards, when the output chamber (36) is manually compressed, it causes cleansed wound exudate to be forced through the annular chamber (16), and thence through the porous film (17) back into the wound.

Referring to FIGS. 5 to 7 and 10, the apparatus (1) in each comprises a cleansing means (4), which comprises a chamber (5), here a conformable hollow bag, defined by the backing layer (3) and a polymer film (6) that is permeable and permanently attached to the proximal face of the backing layer (3).

It sits under the domed backing layer (3) in the underlying wound in use, and contains a cleansing fluid absorbed in a resiliently flexible foam (41).

FIGS. 5 to 7 and 10 show different methods of moving wound exudate in and out of the cleansing means (4).

Figure 5:
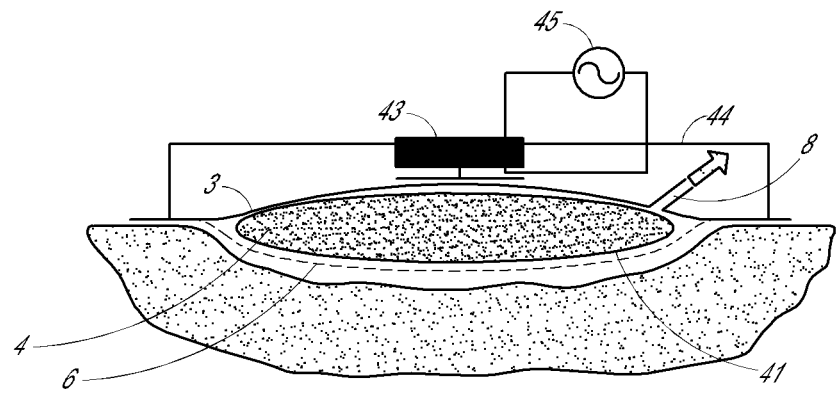
FIG. 5 is a cross-sectional view of an apparatus for cleansing a wound according to the first aspect of the present invention, the apparatus with a single-phase means for wound exudate cleansing, and a circulating system, in which it/they pass in only one direction.

In FIG. 5, an electromechanical oscillator or piezoelectric transducer (43) is mounted centrally in contact with the backing layer (3) on a rigid frame (44) mounted at the periphery of the backing layer (3), and is connected electrically to an appropriate alternating electrical power source (45) (shown schematically). The chamber (5) is provided with a bleed valve (8). If exudate build up under the backing layer (3) becomes excessive during use, the bleed valve (8) may be opened and excess fluid vented off, and any excess pressure relieved.

Figure 6:
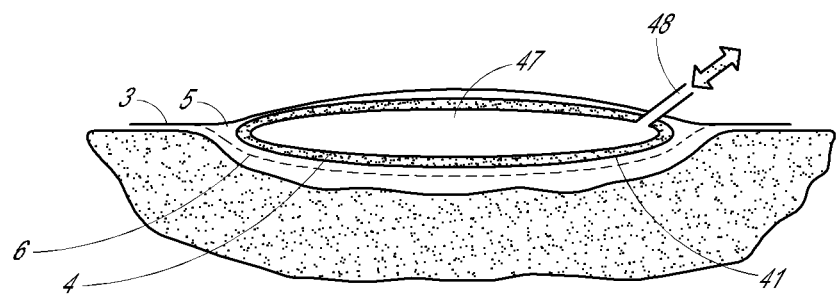
FIG. 6 is a cross-sectional view of an apparatus for cleansing a wound according to the first aspect of the present invention, the apparatus with a single-phase means for wound exudate cleansing, and a reversing system, in which the wound exudate and optionally irrigant passes through the cleansing means one or more times at least once in opposing directions.

In FIG. 6, the foam (41) has a resiliently flexible, balloon core (47), which is inflatable and deflatable with a fluid, such as a gas, e.g. air or nitrogen, or a liquid, such as water or saline, to apply varying pressure to the chamber (5) via an inlet and outlet pipe (48) mounted at the periphery of the backing layer (3).

The pipe (48) is connected to a suitable moving device (58) (not shown) for moving the inflating fluid in and out of the core (47) and thus to move wound exudate in and out of the cleansing means (4). Such a device is suitably one that is capable of optionally pulsed, reversible fluid movement.

It may in particular be a small peristaltic pump or diaphragm pump, e.g. preferably a battery-driven miniature portable diaphragm or peristaltic pump, e.g. mounted centrally on the backing layer (3) above the chamber (5) and is releasably attached to the backing layer (3).

Figure 7:
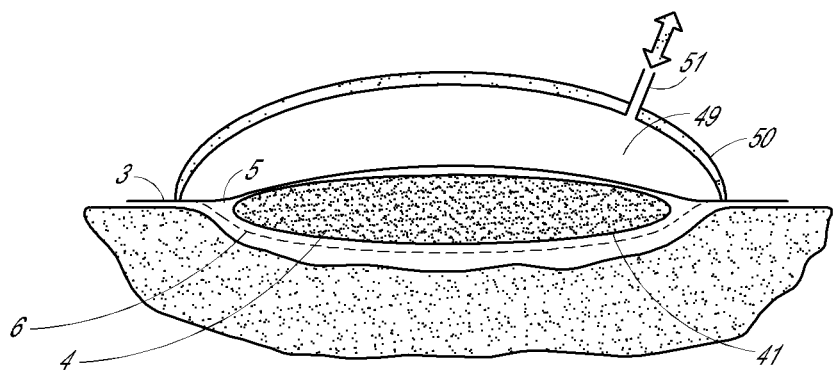
FIG. 7 is a cross-sectional view of an apparatus for cleansing a wound according to the first aspect of the present invention, the apparatus with a single-phase means for wound exudate cleansing, and a reversing system, in which the wound exudate and optionally irrigant passes through the cleansing means one or more times at least once in opposing directions.

FIG. 7 shows a variant of the apparatus (1) of FIG. 6. The resiliently flexible, balloon core (47) under the backing layer (3) is replaced by a resiliently flexible, balloon chamber (49), defined by the backing layer (3) and a rigid polymer dome (50) that is impermeable and permanently attached to the distal face of the backing layer (3).

The balloon chamber (49), defined by the backing layer (3) and the rigid polymer dome (50) is also inflatable and deflatable with a fluid, such as a gas, e.g. air or nitrogen, or a liquid, such as water or saline, to apply varying pressure to the chamber (5) via an inlet and outlet pipe (51) mounted at the periphery of the backing dome (50).

A suitable moving device (58) (not shown) is used for moving the inflating fluid in and out of the balloon chamber (49) and thus to move wound exudate in and out of the cleansing means (4), as noted in respect of FIG. 6, and may be mounted on the dome (50) rather than the backing layer (3).

Figure 10:
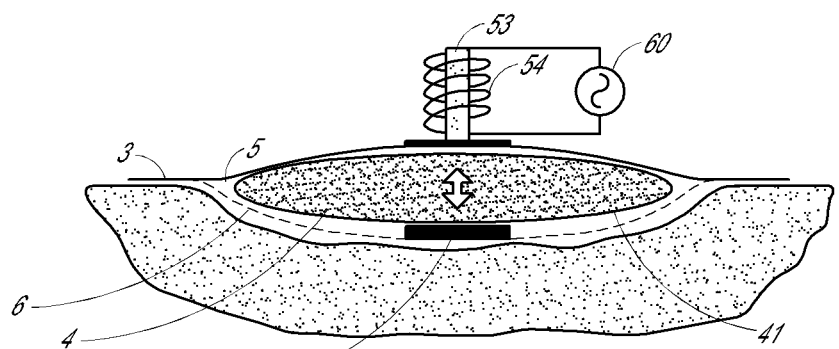
FIG. 10 is a cross-sectional view of an apparatus for cleansing a wound according to the first aspect of the present invention, the apparatus with a single-phase means for wound exudate cleansing.

In FIG. 10, an electromagnetic solenoid core (53) within an electrical coil (54) is mounted centrally in contact with the backing layer (3) on a rigid flange (55). The electrical coil (54) is connected electrically to an appropriate alternating electrical power source (60) (shown schematically).

The chamber (5) is provided at its base with an attached disc (56) of a ferromagnetic material sheathed from the wound exudate and cleansing fluid.

As the direction of current flow alternates, the solenoid core follows, and so compresses and releases the chamber (5), and hence causes wound exudate to be forced to and fro through the cleansing means (4).

Figure 8:
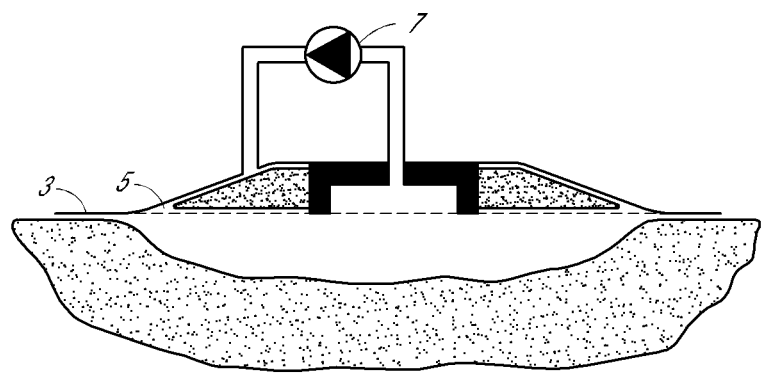
FIG. 8 is a cross-sectional view of an apparatus for cleansing a wound according to the first aspect of the present invention, the apparatus with a single-phase means for wound exudate cleansing, and a circulating system, in which it/they pass in only one direction.
Figure 9:
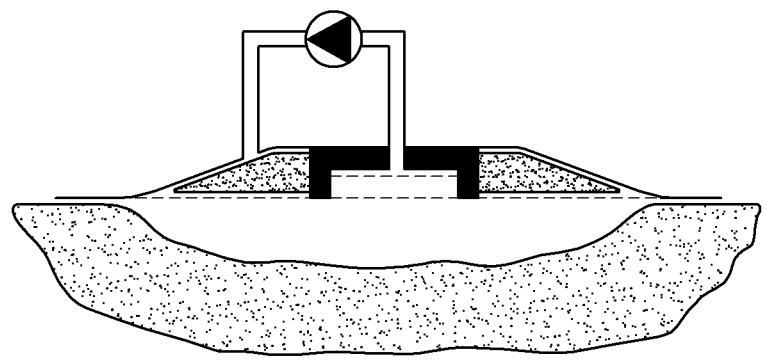
FIG. 9 is a cross-sectional view of an apparatus for cleansing a wound according to the first aspect of the present invention, the apparatus with a single-phase means for wound exudate cleansing, and a circulating system, in which it/they pass in only one direction.

FIGS. 8 and 9 show a variant of the apparatus (1) of FIGS. 1 and 4. The moving device (7) in both cases that respectively replaces the syringe and the press-button pump is a small peristaltic pump or diaphragm pump. It is preferably a battery-driven miniature portable diaphragm or peristaltic pump, e.g. mounted centrally on the backing layer (3) above the chamber (5) and is releasably attached to the backing layer (3).

Figure 11:
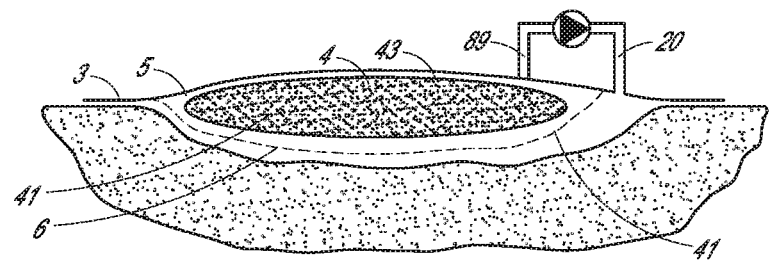
FIG. 11 is a cross-sectional view of an apparatus for cleansing a wound according to the first aspect of the present invention, the apparatus with a single-phase means for wound exudate cleansing, and a circulating system, in which it/they pass in only one direction.

FIG. 11 shows apparatus with a single-phase means for wound exudate cleansing in which the wound exudate passes through the cleansing means one or more times in only one direction. It is similar in structure to the apparatus shown in FIGS. 5 to 7 and 10.

The apparatus (1) comprises a cleansing means (4), which comprises a chamber (5), here a conformable hollow bag, defined by the backing layer (3) and a polymer film (6) that is permeable and permanently attached to the proximal face of the backing layer (3). It contains a cleansing fluid absorbed in a resiliently flexible foam (41).

The resiliently flexible foam (41) is contained in a permeable membrane (43) and contains a material for sequestering deleterious materials from the wound exudate.

These integers form the cleansing means (4).

An outlet pipe (69) passes centrally through the backing layer (3) and communicates between the interior of the chamber (5) and a pump, e.g. preferably a battery-driven miniature portable diaphragm or peristaltic pump, e.g. mounted centrally on the backing layer (3) above the chamber (5) and releasably attached to the backing layer (3).

An inlet pipe (20) passes peripherally through the backing layer (3) and communicates between the wound space and the pump.

In use, wound exudate is moved by the pump (7) through the cleansing means (4), and the foam (41) sequesters deleterious materials from the wound exudate.

FIG. 12 shows apparatus with a two-phase means for wound exudate cleansing in which the cleansing phase moves.

Figure 12A:
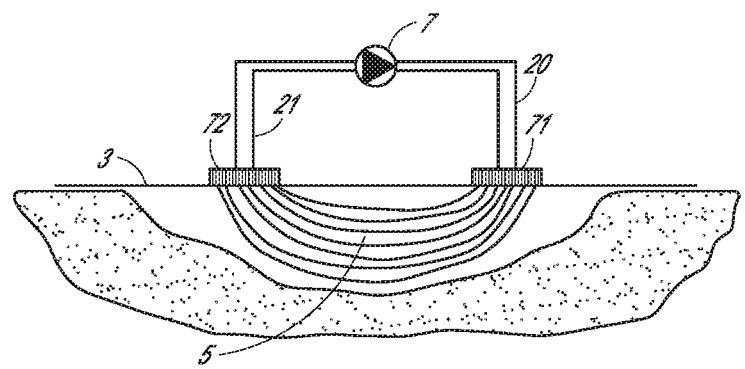
FIG. 12a is a cross-sectional view of an apparatus for cleansing a wound according to the first aspect of the present invention, with a two-phase means for wound exudate cleansing, in which the cleansing phase passes through the cleansing means.

FIG. 12*a* shows apparatus in which the only the cleansing phase moves.

Figure 12B:
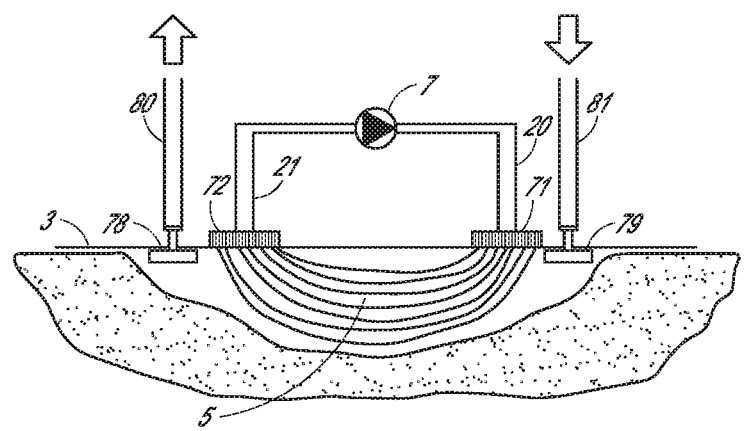
FIG. 12b is a cross-sectional view of an apparatus for cleansing a wound according to the first aspect of the present invention, with a two-phase means for wound exudate cleansing, in which the cleansing phase passes through the cleansing means.

FIG. 12*b* shows apparatus in which the cleansing phase and the wound exudate phase move.

In both Figures, the apparatus (1) comprises a cleansing means (4), which comprises a chamber (5), here in the form of tubules in an array under the backing layer (3) between a first boss (71) and a second boss (72) both mounted in the backing layer (3). The tubules are made from a polymer membrane that is selectively permeable to deleterious materials in the wound exudate, and contain a dialysate fluid.

An inlet pipe (20) passes from the first boss (71) and communicates between the interior of the chamber (5) and a pump (7), e.g. preferably a battery-driven miniature portable diaphragm or peristaltic pump, e.g. mounted centrally on the backing layer (3) above the chamber (5) and releasably attached to the backing layer (3). An outlet pipe (21) passes from the second boss (72) and communicates between the interior of the chamber (5) and the pump (7).

In use, dialysate fluid is moved by the pump (7) through the cleansing means (4), and it removes deleterious materials from the wound exudate.

In FIG. 12*b*, a third boss (78) with a wound exudate outlet passing centrally through it and a fourth boss (79) with a wound exudate inlet passing centrally through it are both mounted peripherally and mutually diametrically opposed in the backing layer (3).

A wound exudate outlet tube (80) is connected to the third boss (78) and communicates between the interior of the wound and the inlet of a second pump (82) (not shown), e.g. preferably a battery-driven miniature portable diaphragm or peristaltic pump, mounted centrally on the backing layer (3).

A wound exudate inlet tube (81) is connected to the fourth boss (79) and communicates between the interior of the wound and the outlet of the second pump.

In use, not only is dialysate fluid moved by the first pump (7) through the cleansing means (4), where it removes deleterious materials from the wound exudate, but the wound exudate phase is moved under the backing layer (3) through the wound space by the second pump in a counter-current direction to enhance the removal from the wound exudate.

Figure 13:
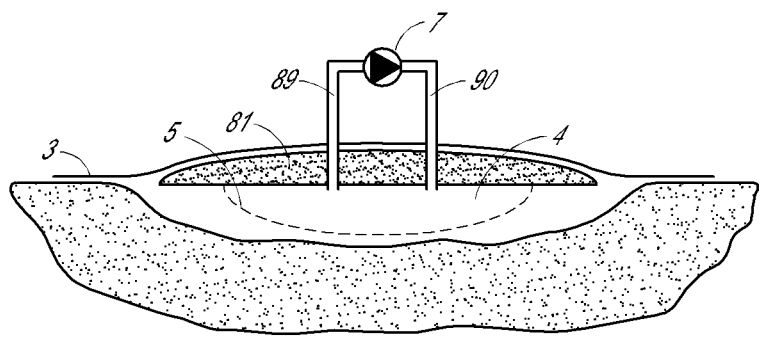
FIG. 13 is a cross-sectional view of an apparatus for cleansing a wound according to the first aspect of the present invention, with a two-phase means for wound exudate cleansing, in which the cleansing phase passes through the cleansing means.

FIG. 13 shows apparatus with a two-phase means for wound exudate cleansing in which the cleansing phase moves.

The apparatus (1) comprises a cleansing means (4), which comprises a chamber (5), here in the form of bag under the backing layer (3) and under a foam filler (81).

This bag is made from a polymer membrane and contains a dialysate fluid, which contains a material as a solute or disperse phase species that is for sequestering or degrading deleterious materials from the wound exudate. The membrane is chosen to be selectively permeable to allow perfusion of deleterious material species targeted for sequestration or destruction from the wound exudate into the dialysate, but not to allow any significant amounts of antagonist in the dialysate fluid phase to diffuse freely out of the dialysate into the wound fluid.

An outlet pipe (89) passes through the backing layer (3) and communicates between the interior of the chamber (5) and a pump, e.g. preferably a battery-driven miniature portable diaphragm or peristaltic pump, e.g. mounted centrally on the backing layer (3) above the chamber (5) and releasably attached to the backing layer (3). An inlet pipe (90) passes peripherally through the backing layer (3) and communicates between the chamber (5) and the pump.

In use, dialysate is moved by the pump (7) through the cleansing means (4). Deleterious material species targeted for sequestration or destruction from the wound exudate into the dialysate, where the antagonist in the dialysate fluid phase removes deleterious materials from the wound exudate, without diffusing out into the exudate.

Figure 14:
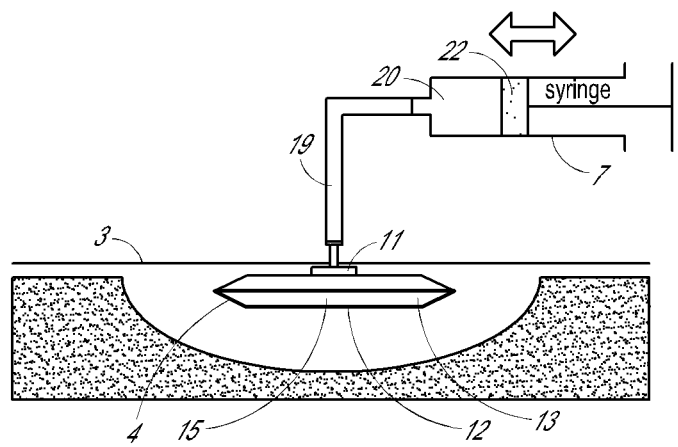
FIG. 14 is a cross-sectional view of an apparatus for cleansing a wound according to the first aspect of the present invention, the apparatus with a single-phase means for wound exudate cleansing, and a reversing system, in which the wound exudate and optionally irrigant passes through the cleansing means one or more times at least once in opposing directions.

In FIG. 14, a reversing system is shown (wound exudate passes through the cleansing means at least once in opposing directions) that is similar in structure to the apparatus shown in FIGS. 1 and 3.

The microbe-impermeable polyurethane film backing layer (3), formed by solution casting or extrusion, bears a centrally attached proximally projecting boss (11) with a luer for connection to a mating end of a fluid supply and offtake tube (19), which communicates between the interior of the boss (11) and a syringe barrel (20), which is part of a syringe moving device (7).

A lower porous film (12) and an intermediate porous membrane (13), both made of permeable polyurethane membrane with small apertures or pores, define a cleansing chamber (15), which contains a solid particulate (not shown). This is for sequestering deleterious materials from, but initially separated from, the wound exudate. These integers, with a coextensive impermeable upper sheet (24) with an upper aperture adapted to register with the conduit in the boss (11), form an upper chamber (25), and all together form the cleansing means (4). This is mounted on the lower face of the boss (11) with the upper aperture in register with the conduit in the boss (11).

In use, movement of the syringe plunger (22) sucks and forces wound exudate to and fro through the cleansing means (4).

Figure 15:
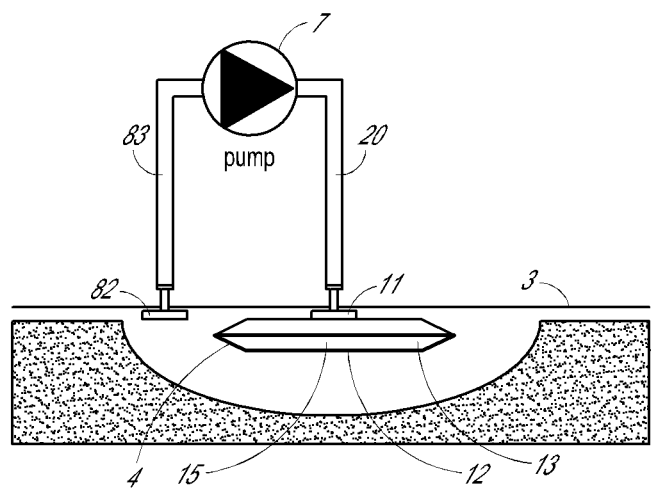
FIG. 15 is a cross-sectional view of an apparatus for cleansing a wound according to the first aspect of the present invention, the apparatus with a circulating system, in which it/they pass in only one direction.

The apparatus (1) in FIG. 15 is a circulating system (wound exudate passes through the cleansing means one or more times in only one direction). It is a variant of the apparatus (1) of FIGS. 8 and 9.

The microbe-impermeable polyurethane film backing layer (3), formed by solution casting, bears a centrally mounted proximally projecting boss (11) with a uniform cylindrical-bore conduit through it and a luer for connection to a mating end of a fluid supply tube (20), which communicates between the interior of the boss (11) and the outlet of moving device (7).

The moving device (7) is a battery-driven miniature portable diaphragm or peristaltic pump, mounted centrally on the backing layer (3) and is releasably attached to the backing layer (3).

A second proximally projecting boss (82) with a luer for connection to a mating end of a fluid offtake tube (83) is mounted peripherally on the backing layer (3). The fluid offtake tube (83) communicates between the wound space and the inlet of the pump (7).

A lower porous film (12) and an intermediate porous membrane (13), both made of permeable polyurethane membrane with small apertures or pores, define a cleansing chamber (15), which contains a solid particulate (not shown) for sequestering deleterious materials from, but initially separated from, the wound exudate. These integers, with a coextensive impermeable upper sheet (24) with an upper aperture adapted to register with the conduit in the boss (11), form an upper chamber (25), and all together form the cleansing means (4). This is mounted on the lower face of the boss (11) with the upper aperture in register with the conduit in the boss (11).

In use, wound exudate is moved by the pump (7) through the cleansing means (4), and the particulate (not shown) sequesters deleterious materials from the wound exudate The use of the apparatus of the present invention will now be described by way of example only in the following Examples:

Example 1

Cleansing Fe(II) from Aqueous Solution with the Apparatus of FIG. 1: Single-Phase Hand-Syringe Pumped Dressing Containing Solid Sequestrant (Cadexomer-Desferrioxamine)

A hand-syringe pumped dressing as shown in FIG. 14 was made up. The cleansing chamber (15) contains a solid particulate (not shown) desferrioxamine supported on Cadexomer (50 mg) to sequester and remove deleterious Fe(II) ions from surrogate exudate.

The porous film (12) and a permeable membrane (13), both made of Porvair permeable membrane, are chosen to allow perfusion and flow under syringe pumping through the cleanser but to contain the solid reagent.

In triplicate, the dressing as shown in FIG. 1 was applied to a 9.60 ml capacity circular wound cavity (cast in Perspex) containing an aqueous solution of ferrous chloride tetrahydrate (Aldrich) (9.60 ml, 200 µmolar).

The solution was repeatedly completely withdrawn and completely reinjected using the device syringe. At each withdrawal, a 100 microlitre aliquot of solution was assayed using a ferrozine assay as follows: each 100 ul aliquot was added immediately to a 1.5 ml capacity, 1 cm path-length UV cuvette containing 1 ml Ferrozine stock solution (73.93 mg Ferrozine was made up to 250 ml in distilled water (600 uM)). Absorbance (562 nm) readings were taken after at least 5 min. incubation. The absorbance was measured using UNICAM UV4-100 UV-Vis spectrophotometer V3.32 (serial no. 022405).

Six passes were made in total, at four minute intervals. The same method was repeated in the absence of flow (i.e. without syringe pumping through the cleanser) and sampled at equivalent time points.

Results and Conclusions

The resulting iron concentration profiles were averaged and the standard deviations were determined. The Fe(II) concentration is effectively depleted to background level in 3 full cycles (12 minutes). In the control, insignificant concentration change has occurred in the same time period.

The dressing as shown in FIG. 1 effectively sequesters Fe(II) from aqueous solution such as water, saline or wound exudate.

Example 2

Neutralising the pH of an Acidic Solution with the Apparatus of FIG. 15: Single-Phase Recirculating Pumped Dressing Containing Solid Acid Scavenger, Scavengepore® Phenethyl Morpholine.

A recirculating pumped dressing as shown in FIG. 15 was made up. The cleansing chamber (15) contains a solid particulate (not shown) of ScavengePore® phenethyl morpholine (Aldrich) (50 mg), which is a low-swelling macroporous highly crosslinked polystyrene/divinylbenzene ion-exchanger resin matrix, with 200-400 micron particle size, to scavenge and remove protons, which are acidic species which adversely affect the pH in the wound exudate, from surrogate exudate.

The porous film (12) and a permeable membrane (13), both made of Porvair permeable membrane, are chosen to allow perfusion and flow under pumping through the cleanser but to contain the ion-exchange reagent.

In triplicate, 4.80 ml DMEM was In triplicate, Device 2 was applied to a 9.60 ml capacity circular wound cavity (cast in Perspex) containing Dulbecco's Modified Eagles Medium (DMEM) (Sigma) (4.80 ml, pH adjusted to pH 6.6 using hydrochloric acid (0.975 N in water, 75 0). The remaining cavity volume was filled with glass beads. The solution was circulated through the cavity at a flow rate of 2.35 ml min$^{-1}$.

100 µl samples were taken at 5 min. time points up to 40 min, and pH was recorded using a flat-bed pH meter. The same method was repeated in the absence of flow (i.e. no pump circulation of the solution) and sampled at equivalent time points.

Results and Conclusions

The resulting pH profiles were averaged and standard deviations determined. The pH was effectively adjusted to pH 7.4 in 40 min. In the control, a slower change in pH was observed in the same time period to pH 7.

Example 3

Cleansing Elastase from Aqueous Solution by Diffusion Across a Dialysis Membrane with the Apparatus of FIG. 12: Two-Phase Recirculating Pumped Dressing Containing No Reagent A recirculating pumped dressing as shown in FIG. 12 was made up. The cleansing chamber (5) is in the form of tubules made from a polymer membrane that is selectively permeable to a deleterious materials in wound exudate (elastase). These in an array under the backing layer (3) within the wound space between a first boss (71) and a second boss (72) both mounted in the backing layer (3). The tubules contain a dialysate fluid and are in a circuit with a pump (7).

In triplicate, the dressing as shown in FIG. 12 was applied to a 9.60 ml capacity circular wound cavity (cast in Perspex) containing elastase solution (porcine pancreatic elastase, Sigma) (4.80 ml, 0.5 mgml$^{-1}$ in TRIS buffer, pH 8.2, 0.2 M). The remaining cavity volume was filled with glass beads. The inlet and outlet ports were connected to the circulating pump.

The dialysate system was prefilled with TRIS (pH 8.0, 0.2 M). This was circulated through the dressing at a flow rate of 2.35 ml min$^{-1}$. 10 µl samples of the circulating solution were taken at 5 min. time points up to 45 min, and the activity was recorded using a standard N-succinyl-(ala)$_3$-p-nitroanilide colorimetric assay. The same method was repeated in the absence of flow (i.e. no pump circulation of the solution) and sampled at equivalent time points.

Results and Conclusions

The activity of the samples was determined from their absorbances at 405 nm using a UV/Vis spectrometer. Results were averaged and standard deviations determined. Effective transfer of elastase across the dialysis membrane is seen in 45 min. In the control, no effective transfer was observed in the same time period.

Example 4

Cleansing Fe(II) from Aqueous Solution with the Apparatus of FIG. 13: Two-Phase Recirculating Pumped Dressing Containing Liquid Phase Sequestrant (Starch-Desferrioxamine (DFO) Conjugate)

An analogue of the apparatus (1) in FIG. 13 was made up, i.e. with a circulating system (wound exudate passes through the cleansing means one or more times in only one direction) with a two-phase means for wound exudate cleansing in which the cleansing phase moves.

The apparatus (1) comprises a cleansing means (4), which comprises a chamber (5) which is made from a polymer membrane and contains a dialysate fluid, which contains a material as a solute or disperse phase species that is for sequestering or degrading deleterious materials from the wound exudate.

The membrane is chosen to be selectively permeable to allow perfusion of deleterious material species targeted for sequestration or destruction from the wound exudate into the dialysate, but not to allow any significant amounts of antagonist in the dialysate fluid phase to diffuse freely out of the dialysate into the wound fluid.

The analogue is a circuit containing a 0.5-1.0 ml capacity Slide-A-Lyzer dialysis unit, with an upper chamber and a lower chamber in which wound exudate and cleansing fluid respectively are separated from each other by a polymer membrane chosen to have the properties noted above (MWCO 10000).

The lower chamber, through which cleansing fluid passes, has diagonally opposed inlet and outlet ports, which are opened with needles, connected to a circuit of 5 ml capacity containing a dialysate reservoir and a battery-driven miniature portable diaphragm or peristaltic pump. The circuit contains an aqueous high molecular weight starch-DFO conjugate (5 ml, 4 mg/ml).

An aliquot of ferrous chloride tetrahydrate (Aldrich) solution (0.5 ml 3 mM) was placed in the upper cavity of the slide and dialysed with 3.6 ml/min. flow in the circuit and (as a control) in the absence of flow in the circuit.

10 microlitre aliquots were removed for 30 minutes at 5 minutes intervals (including t=0). The 10 microlitre aliquot of solution was assayed using the ferrozine iron(II) determination assay as described in Example 1 above. These experiments were performed in triplicate.

Results and Conclusions

The resulting iron concentration profiles were averaged and standard deviations determined. The Fe(II) concentration was effectively depleted to approximately 50% of the initial level in 30 minutes. Without circuit flow, Fe(II) concentration was depleted to approximately 75% of the starting value in the same time period. The apparatus effectively sequesters Fe(II) from aqueous solution.

What is claimed is:

1. A multi-component wound dressing for treating a wound using a reduced pressure, comprising:
   a wound covering element adapted to be applied to a surface of the skin to cover the wound, thereby forming a wound space, said wound covering element having at least one connector configured to connect to a pressure reducing device and through which reduced pressure can be applied to the wound;
   a sorption unit configured to absorb wound exudate material in the wound space;
   a porous member positioned above the sorption unit in a fluid pathway between the sorption unit and the pressure reducing the porous member configured to prevent passage of wound exudate material from the sorption unit into the at least one connector;
   wherein the wound dressing is configured such that absorbed wound exudate material, when sequestered by the sorption unit, remains in the wound space until the sorption unit is removed; and
   a wound contact layer positioned below the sorption unit.

2. The multi-component dressing of claim 1, further comprising a pressure reducing device connected to the at least one connector.

3. The multi-component dressing of claim 2, further comprising at least one pipe connected to the pressure reducing device.

4. The multi-component dressing of claim 3, wherein the pipe connects to the pressure reducing device through an opening passing through the wound covering element.

5. The multi-component dressing of claim 3, wherein the pipe connects to a boss mounted to the wound covering element at an opening in the wound covering element.

6. The multi-component dressing of claim 2, wherein the pressure reducing device comprises a pump.

7. The multi-component dressing of claim 2, wherein the pump is mounted to the wound covering element.

8. The multi-component dressing of claim 2, wherein the pump is separate from the multi-component dressing.

9. The multi-component dressing of claim 2, wherein the pump is operated by a piezoelectric transducer.

10. The multi-component dressing of claim 1, wherein the dressing has at least one conformable hollow body that contains the sorption unit.

11. The multi-component dressing of claim 10, wherein the conformable hollow body is defined by a membrane which has pores.

12. The multi-component dressing of claim 11, wherein the conformable hollow body has an inflatable and deflatable balloon core.

13. The multi-component dressing of claim 10, wherein a material of the conformable hollow body contains an active substance which has a therapeutic effect on a wound healing process.

14. The multi-component dressing of claim 10, wherein the conformable hollow body is glued to the wound covering element, a periphery being left free at the wound covering element.

15. The multi-component dressing of claim 1, wherein the sorption unit comprises a gel.

16. The multi-component dressing of claim 15, wherein the gel is hydrophilic.

17. The multi-component dressing of claim 15, wherein the gel is cross-linked.

18. The multi-component dressing of claim 15, wherein the gel is a cellulosic gel.

19. The multi-component dressing of claim 1, wherein the dressing comprises a microbial growth inhibitor.

20. The multi-component dressing of claim 19, wherein the microbial growth inhibitor comprises a metal ion chelator.

21. The multi-component dressing of claim 19, wherein the microbial growth inhibitor comprises a pH adjuster.

22. The multi-component dressing of claim 19, wherein the microbial growth inhibitor further comprises a binder or degrader for binding or destroying endotoxins.

23. The multi-component dressing of claim 1, wherein the wound covering element comprises a backing layer having a proximal, wound-facing face and a distal face, the dressing further comprising:
   a chamber defined between the backing layer and the wound contact layer; and
   wherein the sorption unit is contained within the chamber.

24. The multi-component dressing of claim 23, wherein the backing layer, a polymer film and the sorption unit are integral with each other and configured to be simultaneously applied to the wound as a single unit.

25. The multi-component dressing of claim 23, further comprising at least one port integral with the dressing and configured to make a fluidic connection to the at least one connector.

26. The multi-component dressing of claim 1, wherein the sorption unit is attached to the wound covering element.

27. The multi-component dressing of claim 1, wherein the wound covering element comprises an adhesive film configured to be attached to the skin surrounding the wound.

28. The multi-component dressing of claim 1, further comprising a boss positioned above the wound covering element, the boss comprising a filter.

29. A wound dressing for treating a wound using a reduced pressure, said dressing comprising:
   a wound covering element adapted to be applied to a surface of the skin to cover the wound, thereby forming a sealed wound space, said wound covering element having at least one connector configured to connect to a pressure reducing device and through which reduced pressure can be applied to the wound to provide a sub-atmospheric pressure environment in the wound space,
   a pressure reducing device configured to connect to the at least one connector;
   a sorption unit which absorbs wound exudate material in the wound space; wherein
   the absorbed wound exudate material, sequestered by the sorption unit, remains in the wound space until the sorption unit is removed; and the sorption unit, together with the sub-atmospheric pressure environment of the wound space, promotes movement of the wound exudate material to the sorption unit;

a porous member positioned above the sorption unit in a fluid pathway between the sorption unit and the pressure reducing device, the porous member configured to prevent the passage of wound exudate from the sorption unit into the at least one connector; and a wound contact layer positioned below the sorption unit.

* * * * *

UNITED STATES PATENT AND TRADEMARK OFFICE
CERTIFICATE OF CORRECTION

PATENT NO.        : 9,446,178 B2
APPLICATION NO.   : 13/212039
DATED             : September 20, 2016
INVENTOR(S)       : Patrick Lewis Blott et al.

It is certified that error appears in the above-identified patent and that said Letters Patent is hereby corrected as shown below:

On the Title Page

In Column 2 (page 9, item (56)) at Line 56, Under Other Publications, change "Chuvashia" to --Chuvash--.

In Column 1 (page 10, item (56)) at Line 38, Under Other Publications, change "Problemwuden" to --Problemwunden--.

In Column 1 (page 10, item (56)) at Line 66, Under Other Publications, change "Khirugii," to --Khirurgii,--.

In Column 1 (page 10, item (56)) at Line 69, Under Other Publications, change "Khirugii," to --Khirurgii,--.

In Column 2 (page 10, item (56)) at Line 54, Under Other Publications, change "salmoncida:" to --salmonicida:--.

In Column 1 (page 11, item (56)) at Line 37, Under Other Publications, change "Faeculent" to --Feculent--.

In Column 1 (page 12, item (56)) at Line 38, Under Other Publications, change "Pressue" to --Pressure--.

In Column 1 (page 12, item (56)) at Line 57, Under Other Publications, change "Bostom" to --Boston--.

In Column 2 (page 12, item (56)) at Line 7, Under Other Publications, change "Nephroi." to --Nephrol.--.

Signed and Sealed this
Tenth Day of January, 2017

Michelle K. Lee
*Director of the United States Patent and Trademark Office*

CERTIFICATE OF CORRECTION (continued)
U.S. Pat. No. 9,446,178 B2

In the Specification

In Column 1 at Line 58, Change "a)" to --b)--.

In Column 3 at Line 12, After "amounts" insert --,--.

In Column 7 at Line 20, Change "wound," to --wound.--.

In Column 8 at Line 6, Change "fluid." to --fluid,--.

In Column 9 at Line 41, After "layer" insert --,--.

In Column 10 at Line 36, Change "low" to --'low--.

In Column 11 at Line 58, Change "wound.)" to --wound.--.

In Column 12 at Line 53, After "25000 mm2" insert --,--.

In Column 16 at Line 30, Change "the may" to --that may--.

In Column 17 at Line 39, Change "cleaning." to --cleansing.--.

In Column 17 at Line 48, After "on" insert --,--.

In Column 23 at Line 11, Change "2-(3,4-cyclohexyldiol)" to --2-(3,4-cyclohexanediol)--.

In Column 24 at Line 4, Change "cleaning" to --cleansing--.

In Column 25 at Line 43, After "(18)" insert --,--.

In Column 30 at Line 35, After "exudate" insert --,--.

In Column 31 at Line 23, Change "Scavengepore®" to --ScavengePore®--.

In Column 31 at Line 42, Change "75 0)." to --75 μl).--.

In the Claims

In Column 33 at Line 31, In Claim 1, after "reducing" insert --device,--.